US012668812B2

(12) United States Patent
Andre et al.

(10) Patent No.: US 12,668,812 B2
(45) Date of Patent: Jun. 30, 2026

(54) RECOMBINANT VECTORS SUITABLE FOR THE TREATMENT OF IPEX SYNDROME

(71) Applicants: INSERM (Institut National de la Santé et de la Recherche Médicale), Paris (FR); Université de Paris, Paris (FR); Assistance Publique-Hôpitaux de Paris (APHP), Paris (FR); Fondation Imagine, Paris (FR); Université d'Evry-Val-d'Essonne, Evry (FR); Ecole Pratique des Hautes Etudes, Paris (FR); Medizinische Hochschule Hannover, Hannover (DE)

(72) Inventors: Isabelle Andre, Paris (FR); Emmanuelle Six, Paris (FR); Florence Bellier, Paris (FR); Marianne Delville, Paris (FR); Marina Cavazzana, Paris (FR); Mario Amendola, Evry (FR); Axel Schambach, Hannover (DE)

(73) Assignees: INSERM (Institut National de la Santé et de la Recherche Médicale), Paris (FR); Université de Paris, Paris (FR); Assistance Publique-Hôpitaux de Paris (APHP), Paris (FR); Fondation Imagine, Paris (FR); Université d'Evry-Val-d'Essonne, Evry (FR); Ecole Pratique des Hautes Etudes, Paris (FR); Medizinische Hochschule Hannover, Hannover (DE)

( * ) Notice: Subject to any disclaimer, the term of this patent is extended or adjusted under 35 U.S.C. 154(b) by 1132 days.

(21) Appl. No.: 17/295,093

(22) PCT Filed: Nov. 19, 2019

(86) PCT No.: PCT/EP2019/081820
§ 371 (c)(1),
(2) Date: May 19, 2021

(87) PCT Pub. No.: WO2020/104467
PCT Pub. Date: May 28, 2020

(65) Prior Publication Data
US 2022/0017919 A1 Jan. 20, 2022

(30) Foreign Application Priority Data

Nov. 20, 2018 (EP) ..................................... 18306526
Feb. 8, 2019 (EP) ..................................... 19305148

(51) Int. Cl.
*C12N 15/86* (2006.01)
*A61K 40/11* (2025.01)
*A61K 40/22* (2025.01)
*A61K 40/41* (2025.01)
*C07K 14/47* (2006.01)
*C07K 14/705* (2006.01)
*C12N 5/0783* (2010.01)
*A61K 48/00* (2006.01)

(52) U.S. Cl.
CPC .............. *C12N 15/86* (2013.01); *A61K 40/11* (2025.01); *A61K 40/22* (2025.01); *A61K 40/416* (2025.01); *C07K 14/4702* (2013.01); *C07K 14/70578* (2013.01); *C12N 5/0637* (2013.01); *A61K 48/00* (2013.01); *C12N 2740/15043* (2013.01)

(58) Field of Classification Search
CPC .................. C12N 15/86; C12N 5/0637; C12N 2740/15043; A61K 35/17; C07K 14/4702; C07K 14/70578
See application file for complete search history.

(56) References Cited

FOREIGN PATENT DOCUMENTS

WO 2004/094642 A2 11/2004

OTHER PUBLICATIONS

Passerini, Laura, et al. "CD4+ T cells from IPEX patients convert into functional and stable regulatory T cells by FOXP3 gene transfer." Science translational medicine 5.215 (2013): 215ra174-215ra174. (Year: 2013).*
Sladitschek, Hanna L., and Pierre A. Neveu. "Bidirectional promoter engineering for single cell MicroRNA sensors in embryonic stem cells." PloS one 11.5 (2016): e0155177. (Year: 2016).*

(Continued)

*Primary Examiner* — Teresa E Knight
*Assistant Examiner* — Michael Angelo Riga
(74) *Attorney, Agent, or Firm* — WCF IP

(57) ABSTRACT

IPEX (Immune dysregulation Polyendocrinopathy X linked) syndrome is a primary immunodeficiency caused by mutations in the gene encoding the transcription factor forkhead box P3 (FOXP3), which leads to the loss of function of thymus-derived CD4+CD25+ regulatory T (tTreg) cells. Preclinical and clinical studies suggest that T cell gene therapy approaches designed to selectively restore the repertoire of Treg cells by transfer of wild type FOXP3 gene is a promising potential cure for IPEX. However, there is still a need for a vector that can be used efficiently for the preparation of said Treg cells. The inventors thus compared 6 different lentiviral constructs according to 4 criteria (vector titers, level of transduction of human CD4+ T cells, level of expression of FOXP3 and ΔLNGFR genes, degree of correlation between both expression) and selected one construct comprising a bidirectional PGK-EF1a promoter that showed remarkable efficiency.

6 Claims, 3 Drawing Sheets
Specification includes a Sequence Listing.

(56) References Cited

OTHER PUBLICATIONS

Passerini et al.; "CD4(+) T Cells from IPEX Patients Convert into Functional and Stable Regulatory T Cells by FOXP3 Gene Transfer"; Science Translational Medicine, vol. 5, No. 215, Dec. 11, 2013, pp. 102-111.

Samavarchi-Tehrani et al.; "A Versatile Lentiviral Delivery Toolkit for Proximity-dependent Biotinylation in Diverse Cell Types"; Molecular & Cellular Proteomics, vol. 17, No. 11, Nov. 1, 2018, pp. 2256-2269.

Golding et al.; "A bidirectional promoter architecture enhances lentiviral transgenesis in embryonic and extraembryonic stem cells"; Gene Therapy, vol. 18, No. 8, Mar. 10, 2011, pp. 817-826.

BIOCAT GmbH; "Bidirectional EF1/PGK Promoter based pCDH-EF1-MCS-(PGK-GFP) cDNA Cloning and Expression Vector (HIV)", Dec. 31, 2013, retrieved from the internet, www.biocat.com/products/CD811A-1-SBI.

* cited by examiner

SEQUENCE LISTING

```
<160> NUMBER OF SEQ ID NOS: 11

<210> SEQ ID NO 1
<211> LENGTH: 513
<212> TYPE: DNA
<213> ORGANISM: Homo sapiens
```

-continued

<400> SEQUENCE: 1

```
ccacggggtt ggggttgcgc cttttccaag gcagccctgg gtttgcgcag ggacgcggct      60
gctctgggcg tggttccggg aaacgcagcg gcgccgaccc tgggtctcgc acattcttca     120
cgtccgttcg cagcgtcacc cggatcttcg ccgctaccct tgtgggcccc ccggcgacgc     180
ttcctgctcc gccctaagt cgggaaggtt ccttgcggtt cgcggcgtgc cggacgtgac     240
aaacggaagc cgcacgtctc actagtaccc tcgcagacgg acagcgccag ggagcaatgg     300
cagcgcgccg accgcgatgg gctgtggcca atagcggctg ctcagcgggg cgcgccgaga     360
gcagcggccg ggaagggggcg gtgcgggagg cggggtgtgg ggcggtagtg tgggccctgt     420
tcctgcccgc gcggtgttcc gcattctgca agcctccgga gcgcacgtcg gcagtcggct     480
ccctcgttga ccgaatcacc gacctctctc ccc                                  513
```

<210> SEQ ID NO 2
<211> LENGTH: 1331
<212> TYPE: DNA
<213> ORGANISM: Homo sapiens

<400> SEQUENCE: 2

```
gagtaattca tacaaaagga ctcgccctg ccttggggaa tcccagggac cgtcgttaaa      60
ctcccactaa cgtagaaccc agagatcgct gcgttcccgc cccctcaccc gcccgctctc     120
gtcatcactg aggtggagaa gagcatgcgt gaggctccgg tgcccgtcag tgggcagagc     180
gcacatcgcc cacagtcccc gagaagttgg ggggaggggt cggcaattga accggtgcct     240
agagaaggtg gcgcggggta aactgggaaa gtgatgtcgt gtactggctc cgccttttc     300 ccgagggtgg gggagaaccg tatataagtg cagtagtcgc cgtgaacgtt ctttttcgca     360
acgggtttgc cgccagaaca caggtaagtg ccgtgtgtgg ttcccgcggg cctggcctct     420
ttacgggtta tggcccttgc gtgccttgaa ttacttccac ctggctgcag tacgtgattc     480
ttgatcccga gcttcgggtt ggaagtgggt gggagagttc gaggccttgc gcttaaggag     540 cccccttcgcc tcgtgcttga gttgaggcct ggcttgggcg ctggggccgc cgcgtgcgaa     600
tctggtggca ccttcgcgcc tgtctcgctg cttttcgataa gtctctagcc atttaaaatt     660
tttgatgacc tgctgcgacg cttttttttct ggcaagatag tcttgtaaat gcgggccaag     720
atctgcacac tggtatttcg gtttttgggg ccgcgggcgg cgacggggcc cgtgcgtccc     780
agcgcacatg ttcggcgagg cggggcctgc gagcgcggcc accgagaatc ggacgggggt     840
agtctcaagc tggccggcct gctctggtgc ctggcctcgc gccgccgtgt atcgccccgc     900
cctgggcggc aaggctggcc cggtcggcac cagttgcgtg agcggaaaga tggccgcttc     960
ccggccctgc tgcagggagc tcaaaatgga ggacgcggcg ctcgggagag cgggcggggtg    1020 agtcacccac acaaaggaaa agggcctttc cgtcctcagc cgtcgcttca tgtgactcca    1080
cggagtaccg ggcgccgtcc aggcacctcg attagttctc gagcttttgg agtacgtcgt    1140
ctttaggttg ggggaggggg ttttatgcga tggagtttcc ccacactgag tgggtggaga    1200
ctgaagttag gccagcttgg cacttgatgt aattctcctt ggaatttgcc cttttttgagt    1260 ttggatcttg gttcattctc aagcctcaga cagtggttca aagtttttttt cttccatttc    1320 aggtgtcgtg a                                                          1331
```

<210> SEQ ID NO 3
<211> LENGTH: 513
<212> TYPE: DNA

<213> ORGANISM: Homo sapiens

<400> SEQUENCE: 3
ggggagagag gtcggtgatt cggtcaacga gggagccgac tgccgacgtg cgctccggag        60
gcttgcagaa tgcggaacac cgcgcgggca ggaacagggc ccacactacc gccccacacc       120
ccgcctcccg caccgcccct tcccggccgc tgctctcggc gcgccccgct gagcagccgc       180
tattggccac agcccatcgc ggtcggcgcg ctgccattgc tccctggcgc tgtccgtctg       240
cgagggtact agtgagacgt gcggcttccg tttgtcacgt ccggcacgcc gcgaaccgca       300
aggaaccttc ccgacttagg ggcggagcag gaagcgtcgc cggggggccc acaagggtag       360
cggcgaagat ccgggtgacg ctgcgaacgg acgtgaagaa tgtgcgagac ccagggtcgg       420
cgccgctgcg tttcccggaa ccacgcccag agcagccgcg tccctgcgca aacccagggc       480
tgccttggaa aaggcgcaac cccaaccccg tgg                                    513

<210> SEQ ID NO 4
<211> LENGTH: 40
<212> TYPE: DNA
<213> ORGANISM: Artificial
<220> FEATURE:
<223> OTHER INFORMATION: Synthetic spacer

<400> SEQUENCE: 4
ttaattaaac gcctaccctc gagtagcttg atatgctagc                             40

<210> SEQ ID NO 5
<211> LENGTH: 1884
<212> TYPE: DNA
<213> ORGANISM: Artificial
<220> FEATURE:
<223> OTHER INFORMATION: Synthetic bidirectionnal promoter

<400> SEQUENCE: 5
ggggagagag gtcggtgatt cggtcaacga gggagccgac tgccgacgtg cgctccggag        60
gcttgcagaa tgcggaacac cgcgcgggca ggaacagggc ccacactacc gccccacacc       120
ccgcctcccg caccgcccct tcccggccgc tgctctcggc gcgccccgct gagcagccgc       180
tattggccac agcccatcgc ggtcggcgcg ctgccattgc tccctggcgc tgtccgtctg       240
cgagggtact agtgagacgt gcggcttccg tttgtcacgt ccggcacgcc gcgaaccgca       300
aggaaccttc ccgacttagg ggcggagcag gaagcgtcgc cggggggccc acaagggtag       360
cggcgaagat ccgggtgacg ctgcgaacgg acgtgaagaa tgtgcgagac ccagggtcgg       420
cgccgctgcg tttcccggaa ccacgcccag agcagccgcg tccctgcgca aacccagggc       480
tgccttggaa aaggcgcaac cccaaccccg tggttaatta aacgcctacc ctcgagtagc       540
ttgatatgct agcgagtaat tcatacaaaa ggactcgccc ctgccttggg gaatcccagg       600
gaccgtcgtt aaactcccac taacgtagaa cccagagatc gctgcgttcc cgccccctca       660
cccgcccgct ctcgtcatca ctgaggtgga gaagagcatg cgtgaggctc cggtgcccgt       720
cagtgggcag agcgcacatc gcccacagtc cccgagaagt tggggggagg ggtcggcaat       780
tgaaccggtg cctagagaag gtggcgcggg gtaaactggg aaagtgatgt cgtgtactgg       840
ctccgccttt ttcccgaggg tggggagaa ccgtatataa gtgcagtagt cgccgtgaac       900 gttcttttc gcaacgggtt tgccgccaga acacaggtaa gtgccgtgtg tggttcccgc       960
gggcctggcc tctttacggg ttatggccct tgcgtgcctt gaattacttc cacctggctg      1020
cagtacgtga ttcttgatcc cgagcttcgg gttggaagtg ggtgggagag ttcgaggcct      1080

-continued

```
tgcgcttaag gagcccttc gcctcgtgct tgagttgagg cctggcttgg gcgctggggc      1140
cgccgcgtgc gaatctggtg gcaccttcgc gcctgtctcg ctgctttcga taagtctcta      1200
gccatttaaa attttgatg acctgctgcg acgcttttt tctggcaaga tagtcttgta       1260
aatgcgggcc aagatctgca cactggtatt tcggtttttg gggccgcggg cggcgacggg      1320
gcccgtgcgt cccagcgcac atgttcggcg aggcggggcc tgcgagcgcg gccaccgaga      1380
atcggacggg ggtagtctca agctggccgg cctgctctgg tgcctggcct cgcgccgccg      1440
tgtatcgccc cgccctgggc ggcaaggctg gcccggtcgg caccagttgc gtgagcggaa      1500
agatggccgc ttcccggccc tgctgcaggg agctcaaaat ggaggacgcg gcgctcggga      1560
gagcgggcgg gtgagtcacc cacacaaagg aaaagggcct ttccgtcctc agccgtcgct      1620
tcatgtgact ccacggagta ccgggcgccg tccaggcacc tcgattagtt ctcgagcttt      1680
tggagtacgt cgtctttagg ttggggggag gggttttatg cgatggagtt tccccacact      1740
gagtgggtgg agactgaagt taggccagct tggcacttga tgtaattctc cttggaattt      1800
gccctttttg agtttggatc ttggttcatt ctcaagcctc agacagtggt tcaaagtttt      1860
tttcttccat ttcaggtgtc gtga                                            1884
```

```
<210> SEQ ID NO 6
<211> LENGTH: 816
<212> TYPE: DNA
<213> ORGANISM: Artificial
<220> FEATURE:
<223> OTHER INFORMATION: Synthetic deltaLNGFR protein

<400> SEQUENCE: 6
atggatggcc ctagactcct ccttctcctg ctgctgggcg tgtcactggg cggagccaaa       60
gaggcctgtc ctaccggcct gtacacacac agcggcgagt gctgcaaggc ctgcaatctg      120
ggagaaggcg tggcccagcc ttgcggcgct aatcagaccg tgtgcgagcc ctgcctggac      180
agcgtgacct ttagcgacgt ggtgtccgcc accgagcctt gcaagccttg taccgagtgt      240
gtgggcctgc agagcatgag cgcccccttg cgtggaagcc gacgatgccg tgtgcagatgc      300 gcctacggct actaccagga cgagacaacc ggcagatgcg aggcctgtag agtgtgcgag      360
gccggatctg gcctggtgtt cagttgtcaa gacaagcaga acaccgtgtg tgaagagtgc      420
cccgacggca cctacagcga cgaggccaat cacgtggacc cctgcctgcc atgcacagtg      480
tgcgaagata ccgagcggca gctgcgcgag tgtaccagat gggccgatgc cgagtgcgaa      540
gagatccctg gcagatggat caccagaagc accccccctg agggcagcga tagcacagcc      600
cctagcaccc aggaacctga ggcccctcct gagcaggatc tgatcgcctc tacagtggcc      660
ggcgtcgtga ccacagtgat gggcagttct cagcccgtcg tgacaagagg caccaccgac      720
aacctgatcc ccgtgtactg cagcatcctg ccgctgtgg tcgtgggcct ggtggcctat      780
atcgccttca gcgcggtggaa ccggggcatc ctgtga                              816
```

```
<210> SEQ ID NO 7
<211> LENGTH: 1296
<212> TYPE: DNA
<213> ORGANISM: Artificial
<220> FEATURE:
<223> OTHER INFORMATION: Synthetic codon optimized FoxP3 sequence

<400> SEQUENCE: 7
atgcccaacc ccagacccgg aaagcctagc gccccttctc tggccctggg accttctcct       60
```

-continued

```
ggcgcctccc catcttggag agccgcccct aaagccagcg atctgctggg agctagaggc        120
cctggcggca cattccaggg cagagatctg agaggcggag cccacgcctc tagcagcagc        180
ctgaatccca tgccccctag ccagctgcag ctgcctacac tgcctctcgt gatggtggcc        240
cctagcggag ctagactggg ccctctgcct catctgcagg ccctgctgca ggacagaccc        300
cacttcatgc accagctgag caccgtggat gcccacgcca gaacacctgt gctgcaggtg        360
caccccctgg aaagccctgc catgatcagc ctgacccctc caaccacagc caccggcgtg        420
ttcagcctga aggccagacc tggactgccc cctggcatca atgtggccag cctggaatgg        480
gtgtcccgcg aacctgccct gctgtgcacc ttccccaatc ccagcgcccc cagaaaggac        540
agcacactgt ctgccgtgcc ccagagcagc tatcccctgc tggctaacgg cgtgtgcaag        600
tggcctggct gcgagaaggt gttcgaggaa cccgaggact tcctgaagca ctgccaggcc        660
gaccatctgc tggacgagaa aggcagagcc cagtgtctgc tgcagcgcga gatggtgcag        720
agcctggaac agcagctggt gctggaaaaa gaaaagctga gcgccatgca ggcccacctg        780
gccggaaaaa tggccctgac aaaggccagc agcgtggcca gctctgacaa gggcagctgc        840
tgcattgtgg ccgctggctc tcagggacct gtggtgcctg cttggagcgg acctagagag        900
gcccccgata gcctgtttgc cgtgcggaga cacctgtggg gcagccacgg caactctacc        960
ttccccgagt tcctgcacaa catggactac ttcaagttcc acaacatgag gccccccttc       1020
acctacgcca ccctgatcag atgggccatt ctggaagccc ccgagaagca gcggaccctg       1080
aacgagatct accactggtt tacccggatg ttcgccttct tccggaacca ccccgccacc       1140
tggaagaacg ccatccggca caatctgagc ctgcacaagt gcttcgtgcg ggtggaaagc       1200
gagaagggcg ccgtgtggac agtggacgag ctggaatttc ggaagaagcg gtcccagagg       1260
cccagccggt gtagcaatcc tacccctggc ccttga                                 1296
```

```
<210> SEQ ID NO 8
<211> LENGTH: 816
<212> TYPE: DNA
<213> ORGANISM: Artificial
<220> FEATURE:
<223> OTHER INFORMATION: Synthetic deltaLNGFRco sequence in reverse
      orientation

<400> SEQUENCE: 8
tcacaggatg cccccggttcc accgcttgaa ggcgatatag gccaccaggc ccacgaccac         60
agcggccagg atgctgcagt acacggggat caggttgtcg gtggtgcctc ttgtcacgac        120
gggctgagaa ctgcccatca ctgtggtcac gacgccggcc actgtagagg cgatcagatc        180
ctgctcagga ggggcctcag gttcctgggt gctaggggct gtgctatcgc tgccctcagg        240
gggggtgctt ctggtgatcc atctgccagg gatctcttcg cactcggcat cggcccatct        300
ggtacactcg cgcagctgcc gctcggtatc ttcgcacact gtgcatggca ggcaggggtc        360
cacgtgattg gcctcgtcgc tgtaggtgcc gtcggggcac tcttcacaca cggtgttctg        420
cttgtcttga caactgaaca ccaggccaga tccggcctcg cacactctac aggcctcgca        480
tctgccggtt gtctcgtcct ggtagtagcg gtaggcgcat ctgcacacgg catcgtcggc        540
ttccacgcaa ggggcgctca tgctctgcag gcccacacac tcggtacaag gcttgcaagg        600
ctcggtggcg gacaccacgt cgctaaaggt cacgctgtcc aggcagggct cgcacacggt        660
ctgattagcg ccgcaaggct gggccacgcc ttctcccaga ttgcaggcct gcagcactc         720 gccgctgtgt gtgtacaggc cggtaggaca ggcctctttg gctccgccca gtgacacgcc        780
```

-continued

```
cagcagcagg agaaggagga gtctagggcc atccat                          816

<210> SEQ ID NO 9
<211> LENGTH: 592
<212> TYPE: DNA
<213> ORGANISM: Artificial
<220> FEATURE:
<223> OTHER INFORMATION: Synthetic WPRE sequence

<400> SEQUENCE: 9
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240 ggttggggca ttgccaccac ctgtcagctc ctttccggga ctttcgcttt ccccctccct   300
attgccacgg cggaactcat cgccgcctgc cttgcccgct gctggacagg gctcggctg   360 ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct ccgcgtctt   540 cgccttcgcc ctcagacgag tcggatctcc ctttgggccg cctccccgcc tg           592

<210> SEQ ID NO 10
<211> LENGTH: 250
<212> TYPE: DNA
<213> ORGANISM: Artificial
<220> FEATURE:
<223> OTHER INFORMATION: Synthetic polyadenylation signal in reverse
      orientation

<400> SEQUENCE: 10
cagatctgat cataatcagc cataccacat ttgtagaggt tttacttgct ttaaaaaacc    60
tcccacacct ccccctgaac ctgaaacata aaatgaatgc aattgttgtt gttaacttgt   120
ttattgcagc ttataatggt tacaaataag gcaatagcat cacaaatttc acaaataagg   180 cattttttc actgcattct agttttggtt tgtccaaact catcaatgta tcttatcatg    240
tctggatctc                                                        250

<210> SEQ ID NO 11
<211> LENGTH: 7690
<212> TYPE: DNA
<213> ORGANISM: Artificial
<220> FEATURE:
<223> OTHER INFORMATION: Synthetic Whole sequence including the 5'and 3'
      LTR sequences

<400> SEQUENCE: 11
ccattgcata cgttgtatcc atatcataat atgtacattt atattggctc atgtccaaca    60
ttaccgccat gttgacattg attattgact agttattaat agtaatcaat tacggggtca   120
ttagttcata gcccatatat ggagttccgc gttacataac ttacggtaaa tggcccgcct   180
ggctgaccgc ccaacgaccc ccgcccattg acgtcaataa tgacgtatgt tcccatagta   240
acgccaatag ggactttcca ttgacgtcaa tgggtggagt atttacggta aactgcccac   300
ttggcagtac atcaagtgta tcatatgcca agtacgcccc ctattgacgt caatgacggt   360
aaatggcccg cctggcatta tgcccagtac atgaccttat gggactttcc tacttggcag   420
tacatctacg tattagtcat cgctattacc atggtgatgc ggttttggca gtacatcaat   480
```

-continued

```
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc ggggtctctc tggttagacc agatctgagc ctgggagctc tctggctaac    720
tagggaaccc actgcttaag cctcaataaa gcttgccttg agtgcttcaa gtagtgtgtg    780
cccgtctgtt gtgtgactct ggtaactaga gatccctcag acccttttag tcagtgtgga    840
aaatctctag cagtggcgcc cgaacaggga cttgaaagcg aaagggaaac cagaggagct    900
ctctcgacgc aggactcggc ttgctgaagc gcgcacggca agaggcgagg ggcggcgact    960
ggtgagtacg ccaaaaattt tgactagcgg aggctagaag agagagatg gtgcgagag   1020 cgtcagtatt aagcggggga gaattagatc gcgatgggaa aaaattcggt taaggccagg   1080
gggaaagaaa aaatataaat taaaacatat agtatgggca agcagggagc tagaacgatt   1140
cgcagttaat cctggcctgt tagaaacatc agaaggctgt agacaaatac tgggacagct   1200
acaaccatcc cttcagacag gatcagaaga acttagatca ttatataata cagtagcaac   1260
cctctattgt gtgcatcaaa ggatagagat aaaagacacc aaggaagctt tagacaagat   1320
agaggaagag caaaacaaaa gtaagaccac cgcacagcaa gcggccgctg atcttcagac   1380
ctggaggagg agatatgagg gacaattgga gaagtgaatt atataaatat aaagtagtaa   1440
aaattgaacc attaggagta gcacccacca aggcaaagag aagagtggtg cagagagaaa   1500
aaagagcagt gggaatagga gctttgttcc ttgggttctt gggagcagca ggaagcacta   1560
tgggcgcagc ctcaatgacg ctgacggtac aggccagaca attattgtct ggtatagtgc   1620
agcagcagaa caatttgctg agggctattg aggcgcaaca gcatctgttg caactcacag   1680
tctggggcat caagcagctc caggcaagaa tcctggctgt ggaaagatac ctaaaggatc   1740
aacagctcct ggggatttgg ggttgctctg gaaaactcat ttgcaccact gctgtgcctt   1800
ggaatgctag ttggagtaat aaatctctgg aacagatttg gaatcacacg acctggatgg   1860
agtgggacag agaaattaac aattacacaa gcttaataca ctccttaatt gaagaatcgc   1920
aaaaccagca agaaaagaat gaacaagaat tattggaatt agataaatgg gcaagtttgt   1980
ggaattggtt taacataaca aattggctgt ggtatataaa attattcata atgatagtag   2040
gaggcttggt aggtttaaga atagtttttg ctgtactttc tatagtgaat agagttaggc   2100
agggatattc accattatcg tttcagaccc acctcccaac cccgagggga cccgacaggc   2160
ccgaaggaat agaagaagaa ggtggagaga gagacagaga cagatccatt cgattagtga   2220
acggatctcg acggtatcgg ttaacttttta aaagaaaagg ggggattggg gggtacagtg   2280
caggggaaag aatagtagac ataatagcaa cagacataca aactaaagaa ttacaaaaac   2340
aaattacaaa aattcaaaat tttatcgatt agaccagaaa tagttcgttt aaaccagatc   2400
tgatcataat cagccatacc acatttgtag aggttttact tgctttaaaa aacctcccac   2460 acctcccct gaacctgaaa cataaaatga atgcaattgt tgttgttaac ttgtttattg   2520
cagcttataa tggttacaaa taaggcaata gcatcacaaa tttcacaaat aaggcatttt   2580
tttcactgca ttctagtttt ggtttgtcca aactcatcaa tgtatcttat catgtctgga   2640
tctcaaatcc ctcggaagct gcgcctgtca tcaattcctg cagcccggtg catgactaat   2700
cagttagcct cccccatctc cctcgactcc tgcaggctat cacaggatgc cccggttcca   2760
ccgcttgaag gcgatatagg ccaccaggcc cacgaccaca gcggccagga tgctgcagta   2820
```

-continued

```
cacggggatc aggttgtcgg tggtgcctct tgtcacgacg ggctgagaac tgcccatcac    2880
tgtggtcacg acgccggcca ctgtagaggc gatcagatcc tgctcaggag gggcctcagg    2940
ttcctgggtg ctaggggctg tgctatcgct gccctcaggg ggggtgcttc tggtgatcca    3000
tctgccaggg atctcttcgc actcggcatc ggcccatctg gtacactcgc gcagctgccg    3060
ctcggtatct tcgcacactg tgcatggcag gcaggggtcc acgtgattgg cctcgtcgct    3120
gtaggtgccg tcgggggcact cttcacacac ggtgttctgc ttgtcttgac aactgaacac    3180
caggccagat ccggcctcgc acactctaca ggcctcgcat ctgccggttg tctcgtcctg    3240
gtagtagccg taggcgcatc tgcacacggc atcgtcggct tccacgcaag gggcgctcat    3300
gctctgcagg cccacacact cggtacaagg cttgcaaggc tcggtggcgg acaccacgtc    3360
gctaaaggtc acgctgtcca ggcagggctc gcacacggtc tgattagcgc cgcaaggctg    3420
ggccacgcct tctcccagat tgcaggcctt gcagcactcg ccgctgtgtg tgtacaggcc    3480
ggtaggacag gcctctttgg ctccgcccag tgacacgccc agcagcagga gaaggaggag    3540
tctagggcca tccatggtgg cacgcgtcgg ggagagaggt cggtgattcg gtcaacgagg    3600
gagccgactg ccgacgtgcg ctccggaggc ttgcagaatg cggaacaccg cgcgggcagg    3660
aacagggccc acactaccgc cccacacccc gcctcccgca ccgccccttc ccggccgctg    3720
ctctcggcgc gccccgctga gcagccgcta ttggccacag cccatcgcgg tcggcgcgct    3780
gccattgctc cctggcgctg tccgtctgcg agggtactag tgagacgtgc ggcttccgtt    3840
tgtcacgtcc ggcacgccgc gaaccgcaag gaaccttccc gacttagggg cggagcagga    3900
agcgtcgccg ggggcccac aagggtagcg gcgaagatcc gggtgacgct gcgaacggac    3960
gtgaagaatg tgcgagaccc agggtcggcg ccgctgcgtt tcccggaacc acgcccagag    4020
cagccgcgtc cctgcgcaaa cccagggctg ccttggaaaa ggcgcaaccc caaccccgtg    4080
gttaattaaa cgcctaccct cgagtagctt gatatgctag cgagtaattc atacaaaagg    4140
actcgcccct gccttgggga atcccaggga ccgtcgttaa actcccacta acgtagaacc    4200
cagagatcgc tgcgttcccg cccctcacc cgcccgctct cgtcatcact gaggtggaga    4260
agagcatgcg tgaggctccg gtgcccgtca gtgggcagag cgcacatcgc ccacagtccc    4320
cgagaagttg gggggagggg tcggcaattg aaccggtgcc tagagaaggt ggcgcggggt    4380
aaactgggaa agtgatgtcg tgtactggct ccgcctttt cccgagggtg ggggagaacc    4440
gtatataagt gcagtagtcg ccgtgaacgt tctttttcgc aacgggtttg ccgccagaac    4500
acaggtaagt gccgtgtgtg gttcccgcgg gcctggcctc tttacgggtt atgggcccttg    4560 cgtgccttga attacttcca cctggctgca gtacgtgatt cttgatcccg agcttcgggt    4620
tggaagtggg tgggagagtt cgaggccttg cgcttaagga gccccttcgc ctcgtgcttg    4680
agttgaggcc tggcttgggc gctggggccg ccgcgtgcga atctggtggc accttcgcgc    4740
ctgtctcgct gctttcgata agtctctagc catttaaaat ttttgatgac ctgctgcgac    4800 gcttttttc tggcaagata gtcttgtaaa tgcgggccaa gatctgcaca ctggtatttc    4860
ggtttttggg gccgcgggcg gcgacggggc ccgtgcgtcc cagcgcacat gttcggcgag    4920
gcggggcctg cgagcgcggc caccgagaat cggacggggg tagtctcaag ctggccggcc    4980
tgctctggtg cctggcctcg cgccgccgtg tatcgccccg ccctgggcgg caaggctggc    5040
ccggtcggca ccagttgcgt gagcggaaag atggccgctt cccggccctg ctgcagggag    5100
ctcaaaatgg aggacgcggc gctcgggaga gcgggcgggt gagtcaccca cacaaaggaa    5160
aagggccttt ccgtcctcag ccgtcgcttc atgtgactcc acggagtacc gggcgccgtc    5220
```

```
caggcacctc gattagttct cgagcttttg gagtacgtcg tctttaggtt gggggggaggg    5280 gttttatgcg atggagtttc cccacactga gtgggtggag actgaagtta ggccagcttg    5340
gcacttgatg taattctcct tggaatttgc ccttttttgag tttggatctt ggttcattct    5400
caagcctcag acagtggttc aaagttttt tcttccattt caggtgtcgt gagggatccg      5460
ccaccatgcc caaccccaga cccggaaagc ctagcgcccc ttctctggcc ctgggacctt    5520
ctcctggcgc ctccccatct tggagagccg cccctaaagc cagcgatctg ctgggagcta    5580
gaggccctgg cggcacattc cagggcagag atctgagagg cggagcccac gcctctagca    5640
gcagcctgaa tcccatgccc cctagccagc tgcagctgcc tacactgcct ctcgtgatgg    5700
tggcccctag cggagctaga ctgggccctc tgcctcatct gcaggccctg ctgcaggaca    5760
gaccccactt catgcaccag ctgagcaccg tggatgccca cgccagaaca cctgtgctgc    5820
aggtgcaccc cctggaaagc cctgccatga tcagcctgac ccctccaacc acagccaccg    5880
gcgtgttcag cctgaaggcc agacctggac tgccccctgg catcaatgtg gccagcctgg    5940
aatgggtgtc ccgcgaacct gccctgctgt gcaccttccc caatcccagc gcccccagaa    6000
aggacagcac actgtctgcc gtgccccaga gcagctatcc cctgctggct aacggcgtgt    6060
gcaagtggcc tggctgcgag aaggtgttcg aggaacccga ggacttcctg aagcactgcc    6120
aggccgacca tctgctggac gagaaaggca gagcccagtg tctgctgcag cgcgagatgg    6180
tgcagagcct ggaacagcag ctggtgctgg aaaaagaaaa gctgagcgcc atgcaggccc    6240
acctggccgg aaaaatggcc ctgacaaagg ccagcagcgt ggccagctct gacaagggca    6300
gctgctgcat tgtggccgct ggctctcagg acctgtggt gcctgcttgg agcggaccta     6360
gagaggcccc cgatagcctg tttgccgtgc ggagacacct gtggggcagc cacggcaact    6420
ctaccttccc cgagttcctg cacaacatgg actacttcaa gttccacaac atgaggcccc    6480
ccttcaccta cgccaccctg atcagatggg ccattctgga agcccccgag aagcagcgga    6540
ccctgaacga gatctaccac tggtttaccc ggatgttcgc cttcttccgg aaccacccg    6600 ccacctggaa gaacgccatc cggcacaatc tgagcctgca caagtgcttc gtgcgggtgg    6660
aaagcgagaa gggcgccgtg tggacagtgg acgagctgga atttcggaag aagcggtccc    6720
agaggcccag ccggtgtagc aatcctaccc ctggcccttg ataggcatgc atatggtcga    6780
caatcaacct ctggattaca aaatttgtga aagattgact ggtattctta actatgttgc    6840
tccttttacg ctatgtggat acgctgcttt aatgcctttg tatcatgcta ttgcttcccg    6900
tatggctttc attttctcct ccttgtataa atcctggttg ctgtctcttt atgaggagtt    6960
gtggcccgtt gtcaggcaac gtggcgtggt gtgcactgtg tttgctgacg caacccccac    7020
tggttggggc attgccacca cctgtcagct cctttccggg actttcgctt tccccctccc    7080
tattgccacg gcggaactca tcgccgcctg ccttgcccgc tgctggacag gggctcggct    7140
gttgggcact gacaattccg tggtgttgtc ggggaaatca tcgtccttc cttggctgct    7200 cgcctgtgtt gccacctgga ttctgcgcgg gacgtccttc tgctacgtcc cttcggccct    7260
caatccagcg gaccttcctt cccgcggcct gctgccggct ctgcggcctc ttccgcgtct    7320
tcgccttcgc cctcagacga gtcggatctc cctttgggcc gcctccccgc ctggaattcg    7380
agctcggtac ctttaagacc aatgacttac aaggcagctg tagatcttag ccacttttta    7440
aaagaaaagg gggactgga agggctaatt cactcccaac gaagacaaga tctgcttttt    7500
gcttgtactg ggtctctctg gttagaccag atctgagcct gggagctctc tggctaacta    7560
```

-continued

```
gggaacccac tgcttaagcc tcaataaagc ttgccttgag tgcttcaagt agtgtgtgcc   7620
cgtctgttgt gtgactctgg taactagaga tccctcagac cctttagtc agtgtggaaa   7680 atctctagca                                                          7690
```

RECOMBINANT VECTORS SUITABLE FOR THE TREATMENT OF IPEX SYNDROME

CROSS-REFERENCE TO RELATED APPLICATIONS

This application is a Rule 371 filing from PCT/EP2019/081820 filed Nov. 19, 2019, which claimed priority to European Applications 18306526.7 filed Nov. 20, 2018 and 19305148.9 filed Feb. 8, 2019.

FIELD OF THE INVENTION

The present invention relates to recombinant vectors suitable for the treatment of IPEX syndrome.

BACKGROUND OF THE INVENTION

IPEX (Immune dysregulation Polyendocrinopathy X linked) syndrome is a primary immunodeficiency caused by mutations in the gene encoding the transcription factor forkhead box P3 (FOXP3) (Wildin et al., 2001) (Bennett et al., 2001), which leads to the loss of function of thymus-derived CD4+CD25+ regulatory T (tTreg) cells (Yagi et al., 2004) (Fontenot et al., 2003) (Hori et al., 2003) (Khattri et al., 2003) (a small subset of circulating CD4+T lymphocytes dedicated to controlling immune responses to self and foreign antigens). In IPEX patients, the absence of a functional Treg cell compartment leads to the development of multiple autoimmune manifestations (including severe enteropathy, type 1 diabetes and eczema) in the first months or years of life (Barzaghi et al., 2012). IPEX syndrome is often fatal early in infancy, and so a prompt diagnosis is essential for starting treatment as soon as possible (before tissue damage spreads to multiple organs).

The current treatments for IPEX syndrome include supportive therapy, immunosuppressive therapy, hormone replacement therapy and HSCT. Unfortunately, these immunosuppressants are usually only partially effective and the dose is often limited by infectious complications and toxicity. Currently, the only cure for IPEX syndrome is allogeneic HSCT. The absence of an HLA-compatible donor for all patients and their poor clinical condition particularly expose them to a risk of mortality. For all these reasons, effective alternative therapeutic approaches are urgently needed.

Based on the outcome of HSCT in this setting, we learned that partial donor chimerism is sufficient for complete remission—provided that full engraftment is achieved in the Treg compartment. In turn, this suggests that a few Tregs could be enough to control autoimmunity in IPEX syndrome (Horino et al., 2014) (Seidel et al., 2009) (Kasow et al., 2011). Moreover, various studies in the mouse (including the scurfy mouse model) have demonstrated the efficacy of the adoptive transfer of healthy Tregs in curing autoimmune diseases (Fontenot et al., 2003) (Mottet et al., 2003) (Tang et al., 2004). The in vivo suppressive capacity of human Tregs obtained after ex vivo expansion has also been demonstrated using humanized mouse model (Wieckiewicz et al., 2010). These various preclinical studies have paved the way for the first clinical trial of the adoptive transfer of ex vivo-expanded Treg cells in two patients with GVHD (Trzonkowski et al., 2009).

Gene therapy of T cells has been successfully developed for TCR or chimeric antigen receptor gene therapy and effectively targets cancer (Bonini et al., 2011) (Kalos and June, 2013) (Provasi et al., 2012). Previous experience of cell therapy with gene-modified T-cells in ADA-SCID (Aiuti et al., 2002) (Blaese et al., 1995) (Muul et al., 2003) indicates that gene-corrected functional T cells persist for more than 15 years after infusion. Furthermore, it has been demonstrated that LV-mediated FOXP3 expression in human CD4 T cells, including from IPEX patients enables the generation of regulatory T cells, which exhibited immunossuppressive activity both with in vitro and in vivo in a xenogenic model of GVHD (Aarts-Riemens et al., 2008) (Allan et al., 2008)(Passerini et al., 2013).

Altogether the results of these preclinical and clinical studies suggest that T cell gene therapy approaches designed to selectively restore the repertoire of Treg cells by transfer of wild type FOXP3 gene is a promising potential cure for IPEX (Aiuti et al., 2012).

However, several prerequisites are absolutely required before any clinical application. First, FOXP3 controls partly the transcriptional signature—and therefore the suppressive function—of Tregs. It has to be expressed at sufficient level to ensure this function and stably to avoid any conversion from Treg to T effector cells and loss of suppressive ability. Secondly, the in vitro generated Tregs must be sorted before their infusion to the patients to avoid any side-effect of non-corrected contaminant effector T cells. As FOXP3 protein is located in the nucleus, it cannot be used to sort FOXP3+ expressing cells. Therefore, it has to be coexpressed with a surface marker. A truncated form of the p75 low-affinity nerve growth factor receptor ($\Delta$LNGFR) with most of the intracytoplasmic tail deleted (from residue 248) has been used as a surface marker in T-cell targeted gene therapy approaches without any side effect (Bonini et al, 1997). Furthermore, the expression of surface $\Delta$LNGFR allows the sorting of transduced cells in clinically applicable conditions. However, to be applicable, the correlation between $\Delta$LNGFR and FOXP3 expression has to be perfect and $\Delta$LNGFR expression should be sufficient to allow the sorting of $\Delta$LNGFR+ cells. The different localization of the two proteins, FOXP3 in the nucleus and $\Delta$LNGFR at the membrane might hamper a strict correlation between both expressions. Thirdly, another obstacle to gene therapy is the efficacy of lentiviral vector production (measured by titrating the vector), which is highly variable and depends on the vector construct and the transgenes. From our knowledge and long-lasting experience, it is impossible to predict the titer. Accordingly, there is still a need for a vector that addresses all these obstacles.

SUMMARY OF THE INVENTION

The present invention relates to recombinant vectors suitable for the treatment of IPEX syndrome. In particular, the present invention is defined by the claims.

DETAILED DESCRIPTION OF THE INVENTION

As shown in the EXAMPLE, the inventors compared 6 different lentiviral constructs according to 4 criteria (vector titers, level of transduction of human CD4+ T cells, level of expression of FOXP3 and $\Delta$LNGFR genes, degree of correlation between both expression) and selected one construct comprising a bidirectional PGK-EF1a promoter that showed remarkable efficiency.

Accordingly, the first object of the present invention relates to a recombinant nucleic acid molecule comprising a bidirectional PGK-EF1a promoter operably linked to a first transgene in one direction and to a second transgene in the opposite direction wherein the first transgene that is under the control of the PGK portion of the bidirectional promoter encodes for a protein that is not constitutively expressed by a T cell and the second transgene that is under the control of the PGK EF1a portion of the bidirectional promoter encodes for a transcription factor.

As used herein, the term "nucleic acid molecule" has its general meaning in the art and refers to a DNA molecule.

As used herein, the terms "promoter" has its general meaning in the art and refers to a segment of a nucleic acid sequence, typically but not limited to DNA that controls the transcription of the nucleic acid sequence to which it is operatively linked. The promoter region includes specific sequences that are sufficient for RNA polymerase recognition, binding and transcription initiation. In addition, the promoter region can optionally include sequences which modulate this recognition, binding and transcription initiation activity of RNA polymerase. The skilled person will be aware that promoters are built from stretches of nucleic acid sequences and often comprise elements or functional units in those stretches of nucleic acid sequences, such as a transcription start site, a binding site for RNA polymerase, general transcription factor binding sites, such as a TATA box, specific transcription factor binding sites, and the like. Further regulatory sequences may be present as well, such as enhancers, and sometimes introns at the end of a promoter sequence.

As used herein, the term "PGK promoter" has its general meaning in the art and refers to the promoter of the gene encoding for phosphoglycerate kinase. An exemplary nucleic acid sequence for the PGK promoter is represented by SEQ ID NO:1.

```
>PGK promoter
                              SEQ ID NO: 1
ccacggggttggggttgcgccttttccaag gcagccctgggtttgcgcagggacgcggct gctctgggcgtggttccgggaaacgcagcg gcgccgaccctgggtctcgcacattcttca cgtccgttcgcagcgtcacccggatcttcg ccgctacccttgtgggcccccggcgacgc ttcctgctccgcccctaagtcgggaaggtt ccttgcggttcgcggcgtgccggacgtgac aaacggaagccgcacgtctcactagtaccc tcgcagacggacagcgccagggagcaatgg cagcgcgccgaccgcgatgggctgtggcca atagcggctgctcagcggggcgcgccgaga gcagcggccgggaaggggcggtgcgggagg cggggtgtgggcggtagtgtgggccctgt tcctgcccgcgcggtgttccgcattctgca agcctccggagcgcacgtcggcagtcggct ccctcgttgaccgaatcaccgacctctctc ccc
```

As used herein, the term EF1a promoter" has its general meaning in the art and refers to the promoter of the gene encoding for elongation factor-1 alpha. An exemplary nucleic acid sequence for the EF1a promoter is represented by SEQ ID NO:2.

```
>EF1a promoter
                              SEQ ID ID NO: 2
gagtaattcatacaaaaggactcgcccctgccttgg ggaatcccagggaccgtcgttaaactcccacta acgtagaacccagagatcgctgcgttcccgcccct cacccgcccgtctctcgtcatcactgaggtggag aagagcatgcgtgaggctccggtgcccgtcagt gggcagagcgcacatcgcccacagtccccgagaagt tggggggaggggtcggcaattgaaccggtgcctagag aaggtggcgcggggtaaactgggaaagtgatg tcgtgactggctccgcctttttcccgagggt ggggagaaccgtatataagtgcagtagtcgccgtga acgttcttttcgcaacgggtttgccgccagaaca caggtaagtgccgtgtgtggttcccgcgggcctg gcctctttacgggttatggcccttgcgtgccttg aattacttccacctggctgcagtacgtgattcttg atcccgagcttcgggttggaagtgggtg ggagagttcgaggccttgcgcttaaggagcccctcgcctc gtgcttgagttgaggcctggcttgggcgctgggg ccgccgcgtgcgaatctggtggcaccttcgcgcct gtctcgctgctttcgataagtctctagccatttaaa atttttgatgacctgctgcgacgcttttttttct ggcaagatagtcttgtaaatgcgggccaagat ctgacacactggtatttcggttttttgggccgcgggcg gcgacggggccccgtgcgtcccagcgcacat gttcggcgaggcggggcctgcgagcgcggccaccgagaa tcggacggggtagtctcaagctggccggcctgct ctggtgcctggcctcgcgccgccgtgtatcgccc cgccctgggcggcaaggctggcccggtcggcacc agttgcgtgagcgaaagatggccgcttcccggcc ctgctgcagggagctcaaaatggaggacgcggcg ctcgggagagcgggcgggtgagtcacccacacaaa ggaaaaggcctttccgtcctcagccgtcgcttcatgt gactccacggagtaccgggcgccgtccaggc acctcgattagttctcgagcttttggagtacgt cgtctttaggttggggggaggggtttttatgcgatgg agtttccccacactgagtgggtggagactgaag ttaaggccagcttggcacttgatgtaattctccttgg aatttgcccttttttgagtttggatcttggttcatt
```

| 5 | 6 |

-continued
gagtaattcatacaaaaggactcgcccctgccttgg tctcaagcctcagacagtggttcaaagtttttttc ttccatttcaggtgtcgtga As used herein, the term "bidirectional promoter" has its general meaning in the art and refers to a promoter which directs transcription of at least 2 transgenes in opposite orientations. Accordingly, a bidirectional promoter according to the present invention directs transcription of a first transgene which lies 5' to 3' in the same 5' to 3' direction as said promoter ("forward orientation") and also directs transcription of another transgene which lies 5' to 3' in a direction opposite from the 5' to 3' direction of said promoter ("reverse orientation"). The bidirectional promoter of the present invention directs gene expression in a bidirectional fashion controlling expression for transgenes placed on both sides of the bidirectional promoter sequence. Thus, the recombinant nucleic acid molecule of the present invention comprises two transgenes, wherein the transcriptional direction (5' to 3') of the PGK and EF1a portions of the PGK-EF1a bidirectional promoter point away from each other (head to head configuration), wherein a first transgene is operably linked in one direction on the left side (i.e. in a reverse orientation), with expression controlled by the PGK portion of the bidirectional promoter, and a second transgene is operably linked in the opposite direction on the right side (i.e. in a forward orientation), with expression controlled by the EF1a portion of the bidirectional promoter.

According to the present invention, the bidirectional promoter of the present invention comprises a first portion that derives from the PGK promoter and a second portion derives from the EF1a promoter.

In some embodiments, the first portion that derives from the PGK promoter comprises a nucleic sequence having at least 80% of identity with the nucleic acid sequence as set forth in SEQ ID NO:3 (i.e. the nucleic acid sequence as set forth in SEQ ID NO:1 that is reverse orientated).

```
>PGK promoter in reverse orientation
                        SEQ ID NO: 3
ggggagagaggtcggtgattcggtcaacga gggagccgactgccgacgtgcgctccggag gcttgcagaatgcggaacaccgcgcgggca ggaacagggcccacactaccgccccacacc ccgcctcccgcaccgccccttcccggccgc tgctctcggcgcgccccgctgagcagccgc tattggccacagcccatcgcggtcggcgcg ctgccattgctccctggcgctgtccgtctg cgagggtactagtgagacgtgcggcttccg tttgtcacgtccggcacgccgcgaaccgca aggaaccttcccgacttaggggcggagcag gaagcgtcgccgggggcccacaagggtag cggcgaagatccgggtgacgctgcgaacgg acgtgaagaatgtgcgagacccagggtcgg cgccgctgcgtttcccggaaccacgcccag
``` agcagccgcgtccctgcgcaaacccagggc tgccttggaaaaggcgcaaccccaacccccg tgg

In some embodiments, the second portion that derives from the EF1a promoter comprises a nucleic sequence having at least 80% of identity with the nucleic acid sequence as set forth in SEQ ID NO:2.

In some embodiments, the first portion that derives from the PGK promoter and the second portion derives from the EF1a promoter are separated by a spacer sequence. In some embodiments, the spacer sequence comprises a nucleic sequence having at least 80% of identity with the nucleic acid sequence as set forth in SEQ ID NO:4.

```
>linker
                        SEQ ID NO: 4
ttaattaaacgcctaccctcgagtagcttgatatgctagc
```

In some embodiments, the bidirectional promoter of the present invention comprises a nucleic acid sequence having at least 80% of identity with the sequence as set forth in SEQ ID NO:5.

```
>bidirectional promoter
SEQ ID NO: 5
ggggagagaggtcggtgattcggtcaacga gggagccgactgccgacgtgcgctccggag gcttgcagaatgcggaacaccgcgcgggca ggaacagggcccacactaccgccccacacc ccgcctcccgcaccgccccttcccggccgc tgctctcggcgcgccccgctgagcagccgc tattggccacagcccatcgcggtcggcgcg ctgccattgctccctggcgctgtccgtctg cgagggtactagtgagacgtgcggcttccg tttgtcacgtccggcacgccgcgaaccgca aggaaccttcccgacttaggggcggagcag gaagcgtcgccgggggcccacaagggtag cggcgaagatccgggtgacgctgcgaacgg acgtgaagaatgtgcgagacccagggtcgg cgccgctgcgtttcccggaaccacgcccag agcagccgcgtccctgcgcaaacccagggc tgccttggaaaaggcgcaaccccaacccccg tggttaattaaacgcctaccctcgagtagc ttgatatgctagc gagtaattcatacaaaaggactcgcccctgcc cttggggaatcccagggaccgtcgttaaactcccact aacgtagaacccagagatcgctgcgttcccgccc ccctcacccgcccgctctcgtcatcactgaggtgga
```

7

-continued

```
gaagagcatgcgtgaggctccggtgcccgtcagt gggcagagcgcacatcgcccacagtccccgagaag ttggggggagggtcggcaattgaaccggtgc ctagagaaggtggcgcggggtaaactgggaaagtgat gtcgtgtactggctccgccttttttcccgaggg tgggggagaaccgtatataagtgcagtagtcgccgtg aacgttctttttcgcaacgggtttgccgccagaacacagg taagtgccgtgtgtggttcccgcgggcct ggcctctttacgggttatggcccttgcgtgccttg aattacttccacctggctgcagtacgtgattctt gatcccgaagcttcgggttagaagtgggtgggg gagttcgaggccttgcgcttaaggagcccttcgcct cgtgcttgaagttgaaggcctggcttgggcgctgggg ccgccgcgtgcgaatctggtggcaccttcgcgcc tgtctcgctgctttcgataagtctctagccatttaaaa ttttttgatgacctgctgcgacgctttttttc tggcaagatagtcttgtaaatgcgggccaagatct gcacactggtatttcggtttttgggaccgcgggc ggcgacgggccgtacgtcccagcacacatgt tcggcgaggcggggcctgcgagcgcggccaccgaga atcggacggggtagtctcaagctggccggcctgc tctggtgcctggcctcgcgccgccgtgtatcgcc ccgccctgggcggcaaggctggcccggtcggcac cagttgcgtgagcggaaagatggccgcttcccggc cctgctgcaggggagctcaaaatggaggacgcggcgct cgggagagcgggcgggtgagtcacccacaa aggaaaaaggccctttccgtcctcagccgtcgcttc atgtgactccacggagtaccgggcgccgtccagg cacctcgattagttctcgagctttttggagtacgtcgt ctttaggttggggggaggggtttatgcgatg gagtttccccacactgagtgggtggagactg aagttaggccagcttggcacttgatgtaattctccttg gaatttgcccttttttgagtttggatcttggttcattct caagcctcagacagtggttcaaagttttttt cttccatttcaggtgtcgtga
```

According to the invention a first nucleic acid sequence having at least 80% of identity with a second nucleic acid sequence means that the first sequence has 80, 81, 82, 83, 84, 85, 86, 87, 88, 89, 90; 91; 92; 93; 94; 95; 96; 97; 98; 99 or 100% of identity with the second nucleic acid sequence.

As used herein, the term "sequence identity," as used herein, has the standard meaning in the art. As is known in the art, a number of different programs can be used to identify whether a nucleic acid sequence has sequence identity or similarity to another nucleic acid sequence. Sequence identity or similarity may be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387 (1984), preferably using the default settings, or by inspection. An example of a useful algorithm is the BLAST algorithm, described in Altschul et al., J. Mol. Biol. 215:403 (1990) and Karlin et al., Proc. Natl. Acad. Sci. USA 90:5873 (1993). A particularly useful BLAST program is the WU-BLAST-2 program which was obtained from Altschul et al., Meth. Enzymol., 266:460 (1996); blast.wustl/edu/ blast/README.html. WU-BLAST-2 uses several search parameters, which are preferably set to the default values. The parameters are dynamic values and are established by the program itself depending upon the composition of the particular sequence and composition of the particular data-base against which the sequence of interest is being searched; however, the values may be adjusted to increase sensitivity.

As used herein, the term "transgene" refers to any nucleic acid that shall be expressed in a mammal cell, in particular a T cell.

In some embodiments, the sequence of the transgenes is codon-optimized. As used herein, the term "codon-optimized" refers to nucleic sequence that has been optimized to increase expression by substituting one or more nucleotides normally present in a codon without changing the amino acid that it encodes by said codon. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription, posttranscriptional regulation and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites as well as polyadenlation sites and instability motifs, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wildtype gene in an otherwise similar cell.

According to the present invention, the first transgene that is under the control of the PGK portion of the bidirectional promoter thus encodes for a protein that is not constitutively expressed by a T cell. Typically, the expression of said protein will be suitable for the cell sorting of the transformed cell with the recombinant nucleic acid molecule of the present invention as described herein after. Typically, said protein is a cell surface marker so that use of binding partners specific for this protein can be used for cell sorting. In some embodiments, the protein is a receptor that will be expressed at the surface of the T cell. In some embodiments, the protein derives from the LNGFR. As used herein, the term "LNGFR" has its general meaning in the art and refers to the low-affinity nerve growth factor receptor. It is a member of the Tumor Necrosis Factor receptor (TNFR) superfamily, and thus anonymously called TNFRSF16. ΔLNGFR consists of 427-amino-acid in overall length, and possesses an extracellular region with four 40 amino acid repeats with 6 cysteins at conserved positions followed by a serine/threonine-rich region, a single transmembrane domain, and a 155 amino acid cytoplasmic domain. LNGFR is expressed in a wide variety of tissues, such as brain, peripheral neurons, Schwann cells, liver, esophagus and oral epithelium and the mesenchyme. However, ΔLNGFR is not expressed in T cells. In some embodiments, the proteins consist of the LNGFR truncated of its intracytoplasmic part. This protein is named "ΔLNGFR". In some embodiments, the first transgene comprises a nucleic acid sequence having at least 80% identity with the nucleic acid sequence as set forth in SEQ ID NO:6.

```
>deltaLNGFRco sequence
                        SEQ ID NO: 6
atggatggccctagactcctccttctcctg ctgctgggcgtgtcactgggcggagccaaa gaggcctgtcctaccggcctgtacacacac agcggcgagtgctgcaaggcctgcaatctg ggagaaggcgtggcccagccttgcggcgct aatcagaccgtgtgcgagccctgcctggac agcgtgacctttagcgacgtggtgtccgcc accgagccttgcaagccttgtaccgagtgt gtgggcctgcagagcatgagcgcccttgc gtggaagccgacgatgccgtgtgcagatgc gcctacggctactaccaggacgagacaacc ggcagatgcgaggcctgtagagtgtgcgag gccggatctggcctggtgttcagttgtcaa gacaagcagaacaccgtgtgtgaagagtgc cccgacggcacctacagcgacgaggccaat cacgtggacccctgcctgccatgcacagtg tgcgaagataccgagcggcagctgcgcgag tgtaccagatgggccgatgccgagtgcgaa gagatccctggcagatggatcaccagaagc accccccctgagggcagcgatagcacagcc cctagcacccaggaacctgaggcccctcct gagcaggatctgatcgcctctacagtggcc ggcgtcgtgaccacagtgatgggcagttct cagccgtcgtgacaagaggcaccaccgac
```

```
aacctgatccccgtgtactgcagcatcctg gccgctgtggtcgtgggcctggtggcctat atcgccttcaagcggtggaaccggggcatc ctgtga
```

In some embodiments, the second transgene that is under the control of the EF1a portion of the bidirectional promoter encodes for a transcription factor. In some embodiments, the transcription factor is FoxP3. As used herein, the term FoxP3 has its general meaning in the art and refers to a transcription factor belonging to the forkhead/winged-helix family of transcriptional regulators. FOXP3 appears to function as a master regulator (transcription factor) in the development and function of regulatory T cells. FoxP3 confers T cells with regulatory function and increases the expression of CTLA-4 and CD25, but decreases IL-2 production by acting as a transcriptional repressor. FoxP3 binds to and suppresses nuclear factor of activated T cells (NFAT) and nuclear factor-kappaB (NFKB) (Bettelli, E. M. et al, 2005, Proc Natl Acad Sci USA 102:5138). In some embodiments, the second transgene comprises a nucleic acid sequence having at least 80% identity with the nucleic acid sequence as set forth in SEQ ID NO:7.

```
>hFoxp3co sequence
                        SEQ ID NO: 7
atgcccaaccccagacccggaaagcctagc gcccttctctggccctgggaccttctcct ggcgcctccccatcttggagagccgcccct aaagccagcgatctgctgggagctagaggc cctggcggcacattccagggcagagatctg agaggcggagcccacgcctctagcagcagc ctgaatcccatgcccctagccagctgcag ctgcctacactgcctctcgtgatggtggcc cctagcggagctagactgggccctctgcct catctgcaggccctgctgcaggacagaccc cacttcatgcaccagctgagcaccgtggat gcccacgccagaacacctgtgctgcaggtg caccccctggaaagccctgccatgatcagc ctgacccctccaaccacagccaccggcgtg ttcagcctgaaggccagacctggactgccc cctggcatcaatgtggccagcctggaatgg gtgtcccgcgaacctgccctgctgtgcacc ttccccaatcccagcgcccccagaaaggac agcacactgtctgccgtgccccagagcagc tatcccctgctggctaacggcgtgtgcaag tggcctggctgcgagaaggtgttcgaggaa cccgaggacttcctgaagcactgccaggcc gaccatctgctggacgagaaaggcagagcc
```

-continued

```
cagtgtctgctgcagcgcgagatggtgcag agcctggaacagcagctggtgctggaaaaa gaaaagctgagcgccatgcaggcccacctg gccggaaaaatggccctgacaaaggccagc agcgtggccagctctgacaagggcagctgc tgcattgtggccgctggctctcagggacct gtggtgcctgcttggagcggacctagagag gcccccgatagcctgtttgccgtgcggaga cacctgtggggcagccacggcaactctacc ttccccgagttcctgcacaacatggactac ttcaagttccacaacatgaggccccccttc acctacgccaccctgatcagatgggccatt ctggaagcccccgagaagcagcggaccctg aacgagatctaccactggtttacccggatg ttcgccttcttccggaaccaccccgccacc tggaagaacgccatccggcacaatctgagc ctgcacaagtgcttcgtgcgggtggaaagc gagaagggcgccgtgtggacagtggacgag ctggaatttcggaagaagcggtcccagagg cccagccggtgtagcaatcctacccctggc ccttga
```

In some embodiments, the nucleic acid molecule of the present invention comprises:
  i) a first nucleic acid sequence having at least 80% of identity with the nucleic acid sequence as set forth in SEQ ID: 8 (which corresponds to the nucleic acid sequence encoding for ΔLNGFR (i.e. SEQ ID NO:6) a in reverse orientation),
  ii) a second nucleic acid sequence having at least 80% of identity with the nucleic acid sequence acid sequence as set forth in SEQ ID NO:5 (which corresponds to the bidirectional promoter) and
  iii) a third nucleic acid sequence having at least 80% of identity with the nucleic acid sequence as set forth in SEQ ID NO:6 (which corresponds to the nucleic acid sequence encoding for FoxP3).

```
>deltaLNGFRco sequence in reverse
orientation
                         SEQ ID NO: 8
tcacaggatgccccggttccaccgcttgaa ggcgatataggccaccaggcccacgaccac agcggccaggatgctgcagtacacggggat caggttgtcggtggtgcctcttgtcacgac gggctgagaactgcccatcactgtggtcac gacgccggccactgtagaggcgatcagatc ctgctcaggaggggcctcaggttcctgggt gctaggggctgtgctatcgctgccctcagg
```

-continued

```
gggggtgcttctggtgatccatctgccagg gatctcttcgcactcggcatcggcccatct ggtacactcgcgcagctgccgctcggtatc ttcgcacactgtgcatggcaggcaggggtc cacgtgattggcctcgtcgctgtaggtgcc gtcggggcactcttcacacacggtgttctg cttgtcttgacaactgaacaccaggccaga tccggcctcgcacactctacaggcctcgca tctgccggttgtctcgtcctggtagtagcc gtaggcgcatctgcacacggcatcgtcggc ttccacgcaagggggcgctcatgctctgcag gcccacacactcggtacaaggcttgcaagg ctcggtggcggacaccacgtcgctaaaggt cacgctgtccaggcagggctcgcacacggt ctgattagcgccgcaaggctgggccacgcc ttctcccagattgcaggccttgcagcactc gccgctgtgtgtgtacaggccggtaggaca ggcctctttggctccgcccagtgacacgcc cagcagcaggagaaggaggagtctagggcc atccat
```

As used herein, the terms "operably linked", or "operatively linked" are used interchangeably herein, and refer to the functional relationship of the nucleic acid sequences with regulatory sequences of nucleotides, such as promoters, enhancers, transcriptional and translational stop sites, and other signal sequences and indicates that two or more DNA segments are joined together such that they function in concert for their intended purposes. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined.

Further regulatory sequences may also be added to the recombinant nucleic acid molecule of the present invention. As used herein, the term "regulatory sequence" is used interchangeably with "regulatory element" herein and refers to a segment of nucleic acid, typically but not limited to DNA, that modulate the transcription of the nucleic acid sequence to which it is operatively linked, and thus acts as a transcriptional modulator. A regulatory sequence often comprises nucleic acid sequences that are transcription binding domains that are recognized by the nucleic acid-binding domains of transcriptional proteins and/or transcription factors, enhancers or repressors etc. In some embodiments, the nucleic acid molecule of the present invention comprises a Woodchuck Hepatitis Virus (WHP) Posttranscriptional Regulatory Element (WPRE) sequence that is a DNA sequence that, when transcribed creates a tertiary structure enhancing expression, by stabilization of the messenger RNA. Typically, the WPRE sequence is inserted downstream to the second transgene (e.g. FoxP3). In some embodiments, the recombinant acid molecule of the present invention comprises a WPRE sequence devoid of X protein open reading frames (ORFs), that allows to remove oncogenic side effect without significant loss of RNA enhancement activity (Schambach, A. et al. Woodchuck hepatitis virus post-transcriptional regulatory element deleted from X protein and promoter sequences enhances retroviral vector titer and expression. Gene Ther. 13, 641-645 (2006)). In some embodiments, the WPRE sequence comprises nucleic acid sequence having at least 80% of identity with the nucleic acid sequence as set forth in SEQ ID NO: 9.

```
>WPRE sequence, LPREm6
[Sequence derived from WPRE
J02442.1 region 1093-1684
with point mutations as
described in Schambach et al
Gene Therapy 2006]
                         SEQ ID NO: 9
AATCAACCTCTGGATTACAAAATTTGTGAA

AGATTGACTGGTATTCTTAACTATGTTGCT

CCTTTTACGCTATGTGGATACGCTGCTTTA

ATGCCTTTGTATCATGCTATTGCTTCCCGT

ATGGCTTTCATTTTCTCCTCCTTGTATAAA

TCCTGGTTGCTGTCTCTTTATGAGGAGTTG

TGGCCCGTTGTCAGGCAACGTGGCGTGGTG

TGCACTGTGTTTGCTGACGCAACCCCCACT

GGTTGGGGCATTGCCACCACCTGTCAGCTC

CTTTCCGGGACTTTCGCTTTCCCCCTCCCT

ATTGCCACGGCGGAACTCATCGCCGCCTGC

CTTGCCCGCTGCTGGACAGGGGCTCGGCTG

TTGGGCACTGACAATTCCGTGGTGTTGTCG

GGGAAATCATCGTCCTTTCCTTGGCTGCTC

GCCTGTGTTGCCACCTGGATTCTGCGCGGG

ACGTCCTTCTGCTACGTCCCTTCGGCCCTC

AATCCAGCGGACCTTCCTTCCCGCGGCCTG

CTGCCGGCTCTGCGGCCTCTTCCGCGTCTT

CGCCTTCGCCCTCAGACGAGTCGGATCTCC

CTTTGGGCCGCCTCCCCGCCTG
```

In some embodiments, the recombinant nucleic acid molecule of the present invention comprises a unidirectional polyadenylation signal sequence inserted downstream to the first transgene (e.g. ΔLNGFR). As used herein, the term "unidirectional polyadenylation signal sequence" has its general meaning in the art and refers to a nucleic acid sequence that is recognized in a directional manner, and that mediates the attachment of a polyadenine stretch to the 3' terminus of the mRNA. Typically, the polyadenylation signal sequence comprises an AATAAA sequence preceded or followed by a GU rich sequence and followed by a CA dinucleotide. In some embodiments, the polyadenylation sequence comprises nucleic acid sequence having at least 80% of identity with the nucleic acid sequence as set forth in SEQ ID NO: 10.

```
>polyadenylation signal in
reverse orientation
                        SEQ ID NO: 10
cagatctgatcataatcagccataccacat ttgtagaggttttacttgctttaaaaaacc tcccacacctcccctgaacctgaaacata aaatgaatgcaattgttgttgttaacttgt ttattgcagcttataatggttacaaataag gcaatagcatcacaaatttcacaaataagg cattttttcactgcattctagttttggtt tgtccaaactcatcaatgtatcttatcatg tctggatctc
```

In some embodiments, the recombinant acid molecule of the present invention comprises a nucleic acid sequence having at least 80% of identity with the nucleic acid sequence as set forth in SEQ ID NO:11.

```
>Whole sequence including the
5' and 3' LTR sequences
                        SEQ ID NO: 11
ccattgcatacgttgtatccatatcataat atgtacatttatattggctcatgtccaaca ttaccgccatgttgacattgattattgact agttattaatagtaatcaattacggggtca ttagttcatagcccatatatggagttccgc gttacataacttacggtaaatggcccgcct ggctgaccgcccaacgacccccgcccattg acgtcaataatgacgtatgttcccatagta acgccaatagggactttccattgacgtcaa tgggtggagtatttacggtaaactgcccac ttggcagtacatcaagtgtatcatatgcca agtacgcccctattgacgtcaatgacggt aaatggcccgcctggcattatgcccagtac atgaccttatgggactttcctacttggcag tacatctacgtattagtcatcgctattacc atggtgatgcggttttggcagtacatcaat gggcgtggatagcggtttgactcacgggga tttccaagtctccacccattgacgtcaat gggagtttgttttggcaccaaaatcaacgg gactttccaaaatgtcgtaacaactccgcc ccattgacgcaaatgggcggtaggcgtgta
```

-continued

```
cggtgggaggtctatataagcagagctcgt ttagtgaaccggggtctctctggttagacc agatctgagcctgggagctctctggctaac tagggaacccactgcttaagcctcaataaa gcttgccttgagtgcttcaagtagtgtgtg cccgtctgttgtgtgactctggtaactaga gatccctcagacccttttagtcagtgtgga aaatctctagcagtggcgcccgaacaggga cttgaaagcgaaagggaaaccagaggagct ctctcgacgcaggactcggcttgctgaagc gcgcacggcaagaggcgaggggcggcgact ggtgagtacgccaaaaattttgactagcgg aggctagaaggagagagatgggtgcgagag cgtcagtattaagcggggggagaattagatc gcgatgggaaaaaattcggttaaggccagg gggaagaaaaaatataaattaaaacatat agtatgggcaagcagggagctagaacgatt cgcagttaatcctggcctgttagaaacatc agaaggctgtagacaaatactgggacagct acaaccatccttcagacaggatcagaaga acttagatcattatataatacagtagcaac cctctattgtgtgcatcaaaggatagagat aaaagacaccaaggaagctttagacaagat agaggaagagcaaaacaaaagtaagaccac cgcacagcaagcggccgctgatcttcagac ctggaggaggagatatgagggacaattgga gaagtgaattatataaatataaagtagtaa aaattgaaccattaggagtagcacccacca aggcaaagagaagagtggtgcagagagaaa aaagagcagtgggaataggagctttgttcc ttgggttcttgggagcagcaggaagcacta tgggcgcagcctcaatgacgctgacggtac aggccagacaattattgtctggtatagtgc agcagcagaacaatttgctgagggctattg aggcgcaacagcatctgttgcaactcacag tctggggcatcaagcagctccaggcaagaa tcctggctgtggaaagatacctaaaggatc aacagctcctggggattttggggttgctctg gaaaactcatttgcaccactgctgtgcctt ggaatgctagttggagtaataaatctctgg aacagatttggaatcacacgacctggatgg
```

-continued

```
agtgggacagagaaattaacaattacacaa gcttaatacactccttaattgaagaatcgc aaaaccagcaagaaaagaatgaacaagaat tattggaattagataaatgggcaagtttgt ggaattggttttaacataacaaattggctgt ggtatataaaattattcataatgatagtag gaggcttggtaggtttaagaatagtttttg ctgtactttctatagtgaatagagttaggc agggatattcaccattatcgtttcagaccc acctcccaaccccgaggggacccgacaggc ccgaaggaatagaagaagaaggtggagaga gagacagagacagatccattcgattagtga acggatctcgacggtatcggttaactttta aaagaaaaggggggattggggggtacagtg caggggaaagaatagtagacataatagcaa cagacatacaaactaaagaattacaaaaac aaattacaaaaattcaaaattttatcgatt agaccagaaatagttcgtttaaaccagatc tgatcataatcagccataccacatttgtag aggttttacttgctttaaaaaacctcccac acctccccctgaacctgaaacataaaatga atgcaattgttgttgttaacttgtttattg cagcttataatggttacaaataaggcaata gcatcacaaatttcacaaataaggcatttt tttcactgcattctagttttggtttgtcca aactcatcaatgtatcttatcatgtctgga tctcaaatccctcggaagctgcgcctgtca tcaattcctgcagcccggtgcatgactaat cagttagcctcccccatctccctcgactcc tgcaggctatcacaggatgccccggttcca ccgcttgaaggcgatataggccaccaggcc cacgaccacagcggccaggatgctgcagta cacggggatcaggttgtcggtggtgcctct tgtcacgacgggctgagaactgcccatcac tgtggtcacgacgccggccactgtagaggc gatcagatcctgctcaggaggggcctcagg ttcctgggtgctaggggctgtgctatcgct gccctcaggggggggtgcttctggtgatcca tctgccagggatctcttcgcactcggcatc ggcccatctggtacactcgcgcagctgccg
```

-continued

```
ctcggtatcttcgcacactgtgcatggcag gcaggggtccacgtgattggcctcgtcgct gtaggtgccgtcggggcactcttcacacac ggtgttctgcttgtcttgacaactgaacac caggccagatccggcctcgcacactctaca ggcctcgcatctgccggttgtctcgtcctg gtagtagccgtaggcgcatctgcacacggc atcgtcggcttccacgcaagggggcgctcat gctctgcaggcccacacactcggtacaagg cttgcaaggctcggtggcggacaccacgtc gctaaaggtcacgctgtccaggcagggctc gcacacggtctgattagcgccgcaaggctg ggccacgccttctcccagattgcaggcctt gcagcactcgccgctgtgtgtgtacaggcc ggtaggacaggcctctttggctccgcccag tgacacgcccagcagcaggagaaggaggag tctagggccatccatggtggcacgcgtcgg ggagagaggtcggtgattcggtcaacgagg gagccgactgccgacgtgcgctccggaggc ttgcagaatgcggaacaccgcgcgggcagg aacagggcccacactaccgccccacacccc gcctcccgcaccgccccttccggccgctg ctctcggcgcgccccgctgagcagccgcta ttggccacagcccatcgcggtcggcgcgct gccattgctccctggcgctgtccgtctgcg agggtactagtgagacgtgcggcttccgtt tgtcacgtccggcacgccgcgaaccgcaag gaaccttcccgacttaggggcggagcagga agcgtcgccggggggcccacaagggtagcg gcgaagatccgggtgacgctgcgaacggac gtgaagaatgtgcgagacccagggtcggcg ccgctgcgtttcccggaaccacgcccagag cagccgcgtccctgcgcaaacccagggctg ccttggaaaaggcgcaaccccaaccccgtg gttaattaaacgcctaccctcgagtagctt gatatgctagcgagtaattcatacaaaagg actcgcccctgccttggggaatcccaggga ccgtcgttaaactcccactaacgtagaacc cagagatcgctgcgttcccgcccctcacc cgcccgctctcgtcatcactgaggtggaga agagcatgcgtgaggctccggtgccgtca
```

-continued

```
gtgggcagagcgcacatcgcccacagtccc cgagaagttggggggagggtcggcaattg aaccggtgcctagagaaggtggcgcgggt aaactgggaaagtgatgtcgtgtactggct ccgcctttttcccgagggtgggggagaacc gtatataagtgcagtagtcgccgtgaacgt tcttttttcgcaacgggtttgccgccagaac acaggtaagtgccgtgtgtggttcccgcgg gcctggcctctttacgggttatggcccttg cgtgccttgaattacttccacctggctgca gtacgtgattcttgatcccgagcttcgggt tggaagtgggtgggagagttcgaggccttg cgcttaaggagcccttcgcctcgtgcttg agttgaggcctggcttgggcgctggggccg ccgcgtgcgaatctggtggcaccttcgcgc ctgtctcgctgctttcgataagtctctagc catttaaaatttttgatgacctgctgcgac gcttttttttctggcaagatagtcttgtaaa tgcgggccaagatctgcacactggtatttc ggttttttggggccgcgggcggcgacggggc ccgtgcgtcccagcgcacatgttcggcgag gcggggcctgcgagcgcggccaccgagaat cggacggggtagtctcaagctggccggcc tgctctggtgcctggcctcgcgccgccgtg tatcgccccgccctgggcggcaaggctggc ccggtcggcaccagttgcgtgagcggaaag atggccgcttcccggccctgctgcagggag ctcaaaatggaggacgcggcgctcgggaga gcgggcgggtgagtcacccacacaaaggaa aagggcctttccgtcctcagccgtcgcttc atgtgactccacggagtaccgggcgccgtc caggcacctcgattagttctcgagcttttg gagtacgtcgtctttaggttgggggggaggg gtttttatgcgatggagtttccccacactga gtgggtggagactgaagttaggccagcttg gcacttgatgtaattctccttggaatttgc cctttttgagtttggatcttggttcattct caagcctcagacagtggttcaaagttttttt tcttccatttcaggtgtcgtgagggatccg ccaccatgcccaacccccagacccggaaagc
```

-continued

```
ctagcgcccttctctggccctgggacctt ctcctggcgcctccccatcttggagagccg cccctaaagccagcgatctgctgggagcta gaggccctggcggcacattccagggcagag atctgagaggcggagcccacgcctctagca gcagcctgaatcccatgccccctagccagc tgcagctgcctacactgcctctcgtgatgg tggcccctagcggagctagactgggccctc tgcctcatctgcaggccctgctgcaggaca gaccccacttcatgcaccagctgagcaccg tggatgcccacgccagaacacctgtgctgc aggtgcacccctggaaagccctgccatga tcagcctgaccoctccaaccacagccaccg gcgtgttcagcctgaaggccagacctggac tgcccoctggcatcaatgtggccagcctgg aatgggtgtcccgcgaacctgccctgctgt gcaccttccccaatcccagcgcccccagaa aggacagcacactgtctgccgtgccccaga gcagctatcccctgctggctaacggcgtgt gcaagtggcctggctgcgagaaggtgttcg aggaacccgaggacttcctgaagcactgcc aggccgaccatctgctggacgagaaaggca gagcccagtgtctgctgcagcgcgagatgg tgcagagcctggaacagcagctggtgctgg aaaaagaaaagctgagcgccatgcaggccc acctggccggaaaaatggccctgacaaagg ccagcagcgtggccagctctgacaagggca gctgctgcattgtggccgctggctctcagg gacctgtggtgcctgcttggagcggaccta gagaggcccccgatagcctgtttgccgtgc ggagacacctgtggggcagccacggcaact ctaccttccccgagttcctgcacaacatgg actacttcaagttccacaacatgaggcccc ccttcacctacgccaccctgatcagatggg ccattctggaagcccccgagaagcagcgga ccctgaacgagatctaccactggtttaccc ggatgttcgccttcttccggaaccacccg ccacctggaagaacgccatccggcacaatc tgagcctgcacaagtgcttcgtgcgggtgg aaagcgagaagggcgccgtgtggacagtgg acgagctggaatttcggaagaagcggtccc
```

-continued

```
agaggcccagccggtgtagcaatcctaccc ctggcccttgataggcatgcatatgGTCGA

CAATCAACCTCTGGATTACAAAATTTGTGA

AAGATTGACTGGTATTCTTAACTATGTTGC

TCCTTTTACGCTATGTGGATACGCTGCTTT

AATGCCTTTGTATCATGCTATTGCTTCCCG

TATGGCTTTCATTTTCTCCTCCTTGTATAA

ATCCTGGTTGCTGTCTCTTTATGAGGAGTT

GTGGCCCGTTGTCAGGCAACGTGGCGTGGT

GTGCACTGTGTTTGCTGACGCAACCCCCAC

TGGTTGGGGCATTGCCACCACCTGTCAGCT

CCTTTCCGGGACTTTCGCTTTCCCCCTCCC

TATTGCCACGGCGGAACTCATCGCCGCCTG

CCTTGCCCGCTGCTGGACAGGGGCTCGGCT

GTTGGGCACTGACAATTCCGTGGTGTTGTC

GGGGAAATCATCGTCCTTTCCTTGGCTGCT

CGCCTGTGTTGCCACCTGGATTCTGCGCGG

GACGTCCTTCTGCTACGTCCCTTCGGCCCT

CAATCCAGCGGACCTTCCTTCCCGCGGCCT

GCTGCCGGCTCTGCGGCCTCTTCCGCGTCT

TCGCCTTCGCCCTCAGACGAGTCGGATCTC

CCTTTGGGCCGCCTCCCCGCCTGGAATTCG

AGCTCGGTACCtttaagaccaatgacttac aaggcagctgtagatcttagccactttta aaagaaaaggggggactggaagggctaatt cactcccaacgaagacaagatctgctttt gcttgtactgggtctctctggttagaccag atctgagcctgggagctctctggctaacta gggaacccactgcttaagcctcaataaagc ttgccttgagtgcttcaagtagtgtgtgcc cgtctgttgtgtgactctggtaactagaga tccctcagacccttttagtcagtgtggaaa atctctagca
```

In some embodiments, the recombinant nucleic acid molecule of the present invention is inserted in a viral vector, and in particular in a retroviral vector.

As used herein, the term "viral vector" refers to a virion or virus particle that functions as a nucleic acid delivery vehicle and which comprises a vector genome packaged within the virion or virus particle.

As used herein, the term "retroviral vector" refers to a vector containing structural and functional genetic elements that are primarily derived from a retrovirus.

In some embodiments, the retroviral vector of the present invention derives from a retrovirus selected from the group consisting of alpharetroviruses (e.g., avian leukosis virus), betaretroviruses (e.g., mouse mammary tumor virus), gammaretroviruses (e.g., murine leukemia virus), deltaretroviruses (e.g., bovine leukemia virus), epsilonretroviruses (e.g., Walley dermal sarcoma virus), lentiviruses (e.g., HIV-1, HIV-2) and spumaviruses (e.g., human spumavirus).

In some embodiments, the retroviral vector of the present invention is a replication deficient retroviral virus particle, which can transfer a foreign imported RNA of a gene instead of the retroviral mRNA. In some embodiments, the retroviral vector of the present invention is a lentiviral vector.

As used herein, the term "lentiviral vector" refers to a vector containing structural and functional genetic elements that are primarily derived from a lentivirus. In some embodiments, the lentiviral vector of the present invention is selected from the group consisting of HIV-1, HIV-2, SIV, FIV, EIAV, BIV, VISNA and CAEV vectors. In some embodiments, the lentiviral vector is a HIV-1 vector.

The structure and composition of the vector genome used to prepare the retroviral vectors of the present invention are in accordance with those described in the art. Especially, minimum retroviral gene delivery vectors can be prepared from a vector genome, which only contains, apart from the recombinant nucleic acid molecule of the present invention, the sequences of the retroviral genome which are non-coding regions of said genome, necessary to provide recognition signals for DNA or RNA synthesis and processing. In some embodiment, the retroviral vector genome comprises all the elements necessary for the nucleic import, integration and the correct expression of the polynucleotide of interest (i.e. the transgene). As examples of elements that can be inserted in the retroviral genome of the retroviral vector of the present invention are at least one (preferably two) long terminal repeats (LTR), such as a LTR5' and a LTR3', a psi sequence involved in the retroviral genome encapsidation, and optionally at least one DNA flap comprising a cPPT (i.e. for lentiviral vector) and a CTS domains. In some embodiments of the present invention, the LTR, is deleted for the promoter and the enhancer of U3. In LTR5' a minimal promoter allowing transcription during vector production while an internal promoter is added to allow expression of the transgene. In particular, the vector is a Self-INactivating (SIN) vector that contains a non-functional or modified 3' Long Terminal Repeat (LTR) sequence. This sequence is copied to the 5' end of the vector genome during integration, resulting in the inactivation of promoter activity in both LTRs. Hence, a vector genome may be a replacement vector in which all the viral coding sequences between the 2 long terminal repeats (LTRs) have been replaced by the recombinant nucleic acid molecule of the present invention.

In some embodiments, the retroviral vector genome is devoid of functional gag, pol and/or env retroviral genes. By "functional" it is meant a gene that is correctly transcribed, and/or correctly expressed. Thus, the retroviral vector genome of the present invention in this embodiment contains at least one of the gag, pol and env genes that is either not transcribed or incompletely transcribed; the expression "incompletely transcribed" refers to the alteration in the transcripts gag, gag-pro or gag-pro-pol, one of these or several of these being not transcribed. In some embodiments, the retroviral genome is devoid of gag, pol and/or env retroviral genes.

In some embodiments the retroviral vector genome is also devoid of the coding sequences for Vif-, Vpr-, Vpu- and Nef-accessory genes (for HIV-1 retroviral vectors), or of their complete or functional genes.

Typically, the retroviral vector of the present invention is non replicative i.e., the vector and retroviral vector genome are not able to form new particles budding from the infected host cell. This may be achieved by the absence in the retroviral genome of the gag, pol or env genes, as indicated in the above paragraph; this can also be achieved by deleting other viral coding sequence(s) and/or cis-acting genetic elements needed for particles formation.

The retroviral vectors of the present invention can be produced by any well-known method in the art including by transfection (s) transient (s), in stable cell lines and/or by means of helper virus. Use of stable cell lines may also be preferred for the production of the vectors (Greene, M. R. et al. Transduction of Human CD34+Repopulating Cells with a Self-Inactivating Lentiviral Vector for SCID-X1 Produced at Clinical Scale by a Stable Cell Line. Hum. Gene Ther. Methods 23, 297-308 (2012).) For instance, the retroviral vector of the present invention is obtainable by a trans-complementation system (vector/packaging system) by transfecting in vitro a permissive cell (such as 293T cells) with a plasmid containing the retroviral vector genome of the present invention, and at least one other plasmid providing, in trans, the gag, pol and env sequences encoding the polypeptides GAG, POL and the envelope protein(s), or for a portion of these polypeptides sufficient to enable formation of retroviral (e.g. lentiviral) particles. As an example, permissive cells are transfected with a) transcomplementation plasmid, lacking packaging signal psi and, the plasmid is optionally deleted of accessory genes vif, nef, vpu and/or vpr, b) a second plasmid (envelope expression plasmid or pseudotyping env plasmid) comprising a gene encoding an envelope protein(s) and c) a plasmid vector comprising a recombinant genome retroviral, optionally deleted from the promoter region of the 3'LTR or U3 enhancer sequence of the 3' LTR, including, between the LTR sequences 5' and 3' retroviral, a psi encapsidation sequence, a nuclear export element (preferably RRE element of HIV or other retroviruses equivalent), comprising the nucleic acid molecule of the present invention and optionally a promoter and/or a nuclear import sequence (cPPT sequence eg CTS) of the RNA. Advantageously, the three plasmids used do not contain homologous sequence sufficient for recombination. Nucleic acids encoding gag, pol and env cDNA can be advantageously prepared according to conventional techniques, from viral gene sequences available in the prior art and databases. The trans-complementation plasmid provides a nucleic acid encoding the proteins retroviral gag and pol. These proteins are derived from a lentivirus, and most preferably, from HIV-1. The plasmid is devoid of encapsidation sequence, sequence coding for an envelope, accessory genes, and advantageously also lacks retroviral LTRs. Therefore, the sequences coding for gag and pol proteins are advantageously placed under the control of a heterologous promoter, eg cellular, viral, etc., which can be constitutive or regulated, weak or strong. It is preferably a plasmid containing a sequence transcomplémentant Δpsi-CMV-gag-pol-PolyA. This plasmid allows the expression of all the proteins necessary for the formation of empty virions, except the envelope glycoproteins. The plasmid transcomplementation may advantageously comprise the TAT and REV genes. Plasmid transcomplementation is advantageously devoid of vif, vpr, vpu and/or nef accessory genes. It is understood that the gag and pol genes and genes TAT and REV can also be carried by different plasmids, possibly separated. In this case, several plasmids are used transcomplementation, each encoding one or more of said proteins. The promoters used in the plasmid transcomplementation, the envelope plasmid and the plasmid vector respectively to promote the expression of gag and pol of the coat protein, the mRNA of the vector genome and the transgene are promoters identical or different, chosen advantageously from ubiquitous promoters or specific, for example, from viral promoters CMV, TK, RSV LTR promoter and the RNA polymerase III promoter such as U6 or H1 or promoters of helper viruses encoding env, gag and pol. For the production of the retroviral vector of the present invention, the plasmids described above can be introduced into competent cells and viruses produced are harvested. The cells used may be any cell competent, particularly eukaryotic cells, in particular mammalian, eg human or animal. They can be somatic or embryonic stem or differentiated. Typically the cells include 293T cells, fibroblast cells, hepatocytes, muscle cells (skeletal, cardiac, smooth, blood vessel, etc.), nerve cells (neurons, glial cells, astrocytes) of epithelial cells, renal, ocular etc. It may also include insect, plant cells, yeast, or prokaryotic cells. It can also be cells transformed by the SV40 T antigen. The genes gag, pol and env encoded in plasmids or helper viruses can be introduced into cells by any method known in the art, suitable for cell type considered. Usually, the cells and the vector system are contacted in a suitable device (plate, dish, tube, pouch, etc. . . . ), for a period of time sufficient to allow the transfer of the vector system or the plasmid in the cells. Typically, the vector system or the plasmid is introduced into the cells by calcium phosphate precipitation, electroporation, transduction or by using one of transfection-facilitating compounds, such as lipids, polymers, liposomes and peptides, etc. The calcium phosphate precipitation or PEI transfection is preferred. The cells are cultured in any suitable medium such as RPMI, DMEM, a specific medium to a culture in the absence of fetal calf serum, etc. Once transfected the retroviral vectors of the present invention may be purified from the supernatant of the cells. Purification of the retroviral vector to enhance the concentration can be accomplished by any suitable method, such as by density gradient purification (e.g., cesium chloride (CsCl)) or by chromatography techniques (e.g., column or batch chromatography). For example, the vector of the present invention can be subjected to two or three CsCl density gradient purification steps. The vector, is desirably purified from cells infected using a method that comprises lysing cells infected with adenovirus, applying the lysate to a chromatography resin, eluting the adenovirus from the chromatography resin, and collecting a fraction containing the retroviral vector of the present invention.

The vector of the present invention is particularly suitable for driving the targeted expression of the transgenes in T cells. According to the present invention, the expression of the transgenes is balanced from both sides of the bidirectional PGK-EF1a promoter. As used herein, "balanced expression", "balance of expression", "expression balance", or "balanced" as it refers to expression, mean that the expression from one side of the bidirectional promoter, as measured for example by different protein expression detection techniques such as Western Blot, FACS analysis, or other assays using luminescence or fluorescence, is comparable to the expression from the other side of the bidirectional promoter. Therefore, balanced expression of the 2 transgenes expressed by a bidirectional PGK-EF1a promoter of the present invention is expected to generate comparable expression of both proteins.

In particular, the vector of the present invention is particularly suitable for obtaining a population of Treg cells that express LNGFR at their cell surface.

Thus a further object of the present invention relates to a method of producing a population of Treg cells, which comprises the step of transfecting or transducing a population of T cells in vitro or ex vivo with the vector of the present invention.

As used herein, the term "T cell" refers to a type of lymphocytes that play an important role in cell-mediated immunity and are distinguished from other lymphocytes, such as B cells, by the presence of a T-cell receptor on the cell surface.

As used herein, the term "regulatory T cells" or "Treg cells" refers to cells that suppress, inhibit or prevent T cells activity. As used herein, Treg cells have the following phenotype at rest CD4+CD25+FoxP3+.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

In some embodiments, the population of T cells is isolated from a subject to whom the genetically modified population of T cells is to be adoptively transferred. In some embodiments, a population of T cells of the present invention are obtained by isolating a population of T-cells from a subject, and by subsequently proceeding with FoxP3 gene transfer ex vivo with the viral vector of the present invention and subsequent immunotherapy of the subject by adoptive transfer of the transduced T cells. Alternatively, the population of T cells is isolated from a different subject, such that it is allogeneic. In some embodiments, the population of T cells is isolated from a donor subject.

Typically, the population of Treg cells is prepared as described in the EXAMPLE. The population of T cells is preactivated in an appropriate culture medium that contains an amount of a recombinant human IL-2 and IL-7 in the presence of soluble anti-CD3 mAb and allogeneic CD3-depleted PBMCs (APCs) that are irradiated. T cells are then infected with the vector of the present invention. LNGFR+ transduced cells were purified by cell sorting. As used herein, the term "cell sorting" is used to refer to a method by which cells are mixed a binding partner (e.g., a fluorescently detectable antibody) in solution. According to the invention, any conventional cell sorting method may be used and typically involve use of anti-LNGFR antibodies. For instance, magnetic bead selection is suitable. Finally, the sorted T cells are expanded in presence of an amount of IL-2 and IL-15.

The population of Treg cells prepared as described above can be utilized in methods and compositions for adoptive immunotherapy in accordance with known techniques, or variations thereof that will be apparent to those skilled in the art based on the instant disclosure.

In particular, the population of Treg cells of the present invention is particularly suitable for the treatment of autoimmune diseases. The Treg cells as prepared by the method of the present invention may be administered for the purpose of suppressing autoimmune activity in a subject. As used herein, the term "autoimmunity" has its general meaning in the art and refers to the presence of a self-reactive immune response (e.g., auto-antibodies, self-reactive T-cells). Autoimmune diseases, disorders, or conditions arise from autoimmunity through damage or a pathologic state arising from an abnormal immune response of the body against substances and tissues normally present in the body. Damage or pathology as a result of autoimmunity can manifest as, among other things, damage to or destruction of tissues, altered organ growth, and/or altered organ function. Types of autoimmune diseases, disorders or conditions include type I diabetes, alopecia areata, vasculitis, temporal arteritis, rheumatoid arthritis, lupus, celiac disease, Sjogrens syndrome, polymyalgia rheumatica, and multiple sclerosis.

In particular, the Treg cells of the present invention are particularly suitable for the treatment of IPEX syndrome.

As used herein, the term "IPEX syndrome" has its general meaning in the art and a disease that results in most cases from mutations in FoxP3. IPEX syndrome usually develops during the first few days or weeks of life and affects exclusively boys. It manifests with the sequential appearance of the triad of enteropathy, autoimmune disease, and cutaneous involvement, but the clinical features and severity of the disease can vary considerably between individuals. Severe autoimmune enteropathy manifests with intractable secretory diarrhea leading to malabsorption, electrolyte disturbance and failure to thrive. Vomiting, ileus, gastritis or colitis can also be observed. Patients also present with autoimmune endocrinopathies, generally insulin-dependent diabetes mellitus (type 1 DM), but also thryroiditis leading to hypothyroidism or hyperthyroidism. Skin involvement consists of a generalized pruriginous eruption resembling eczema, psoriasis, and/or atopic or exfoliative dermatitis. Less frequently, alopecia or onychodystrophy can be observed. Patients may develop autoimmune cytopenias, thrombocytopenia, hemolytic anemia and neutropenia. Autoimmune involvement may also lead to pneumonitis, hepatitis, nephritis, myositis, splenomegaly and/or lymphadenopathy. Local or systemic infections (e.g. pneumonia, *Staphylococcus aureus* infections, candidiasis) may occur but seem to be due to loss of skin and gut barriers, immunosuppressive therapies, and poor nutrition rather than a primary immunodeficiency. IPEX syndrome is caused by mutations in the FOXP3 gene (Xp11.23). More than 20 mutations of FOXP3 are reported in IPEX, and the syndrome is lethal if untreated. Diagnosis is based on clinical examination, family history, and laboratory findings revealing autoimmune enteropathy (anti-enterocyte, harmonin and villin autoantibodies), type 1 DM (antibodies against insulin, pancreatic islet cells, or anti-glutamate decarboxylase), thyroiditis (anti-thyroglobulin and anti-microsome peroxidase antibodies) and cytopenia (anti-platelets and anti-neutrophils antibodies, positive Coombs test). Molecular genetic testing confirms the diagnosis.

Accordingly, a further object of the present invention relates to a method of treating an autoimmune disease (e.g. IPEX syndrome) in a subject in need thereof, comprising administering to the subject a therapeutically effective amount of a population of Treg cells of the present invention.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By a "therapeutically effective amount" is meant a sufficient amount of cells generated with the present invention for the treatment of the disease at a reasonable benefit/ risk ratio applicable to any medical treatment. It will be understood that the total usage of these cells will be decided by the attending physicians within the scope of sound medical judgment. The specific therapeutically effective dose level for any particular subject will depend upon a variety of factors including the age, body weight, general health, sex and diet of the subject; the time of administration, route of administration, and survival rate of the cells employed; the duration of the treatment; drugs used in combination or coincidental with the administered cells; and like factors well known in the medical arts. For example, it is well known within the skill of the art to start doses of cells at levels lower than those required to achieve the desired therapeutic effect and to gradually increase the dosage until the desired effect is achieved.

In some embodiments, the Tregs cells are formulated by first harvesting them from their culture medium, and then washing and concentrating the cells in a medium and container system suitable for administration (a "pharmaceutically acceptable" carrier) in a treatment-effective amount. Typically, the population of Tregs cells of the present invention is administered to the subject in the form of pharmaceutical composition. The pharmaceutical composition may be produced by those of skill, employing accepted principles of treatment. Such principles are known in the art, and are set forth, for example, in Braunwald et al., eds., Harrison's Principles of Internal Medicine, 19th Ed., McGraw-Hill publisher, New York, N.Y. (2015), which is incorporated by reference herein. The pharmaceutical composition may be administered by any means that achieve their intended purpose. For example, administration may be by parenteral, subcutaneous, intravenous, intradermal, intramuscular, intraperitoneal, transdermal, or buccal routes. The pharmaceutical compositions may be administered parenterally by bolus injection or by gradual perfusion over time. The pharmaceutical compositions typically comprises suitable pharmaceutically acceptable carriers comprising excipients and auxiliaries which may facilitate processing of the active compounds into preparations which can be used pharmaceutically. The pharmaceutical compositions may contain from about 0.001 to about 99 percent, or from about 0.01 to about 95 percent of active compound(s), together with the excipient.

The invention will be further illustrated by the following figures and examples. However, these examples and figures should not be interpreted in any way as limiting the scope of the present invention.

FIGURES

Figure 2:
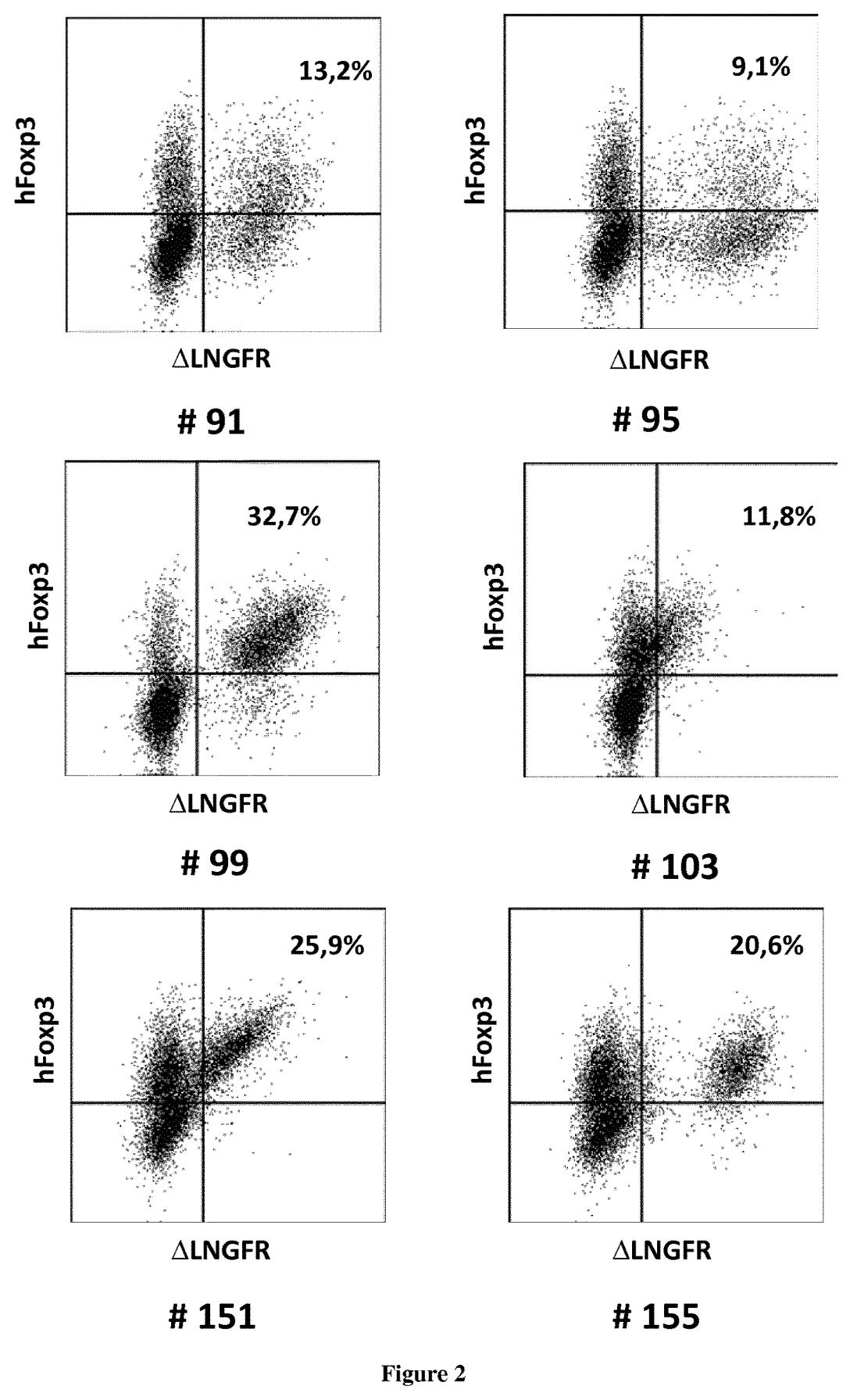

FIG. 2 depicts the flow cytometry analysis at Day 5.

Figure 3:
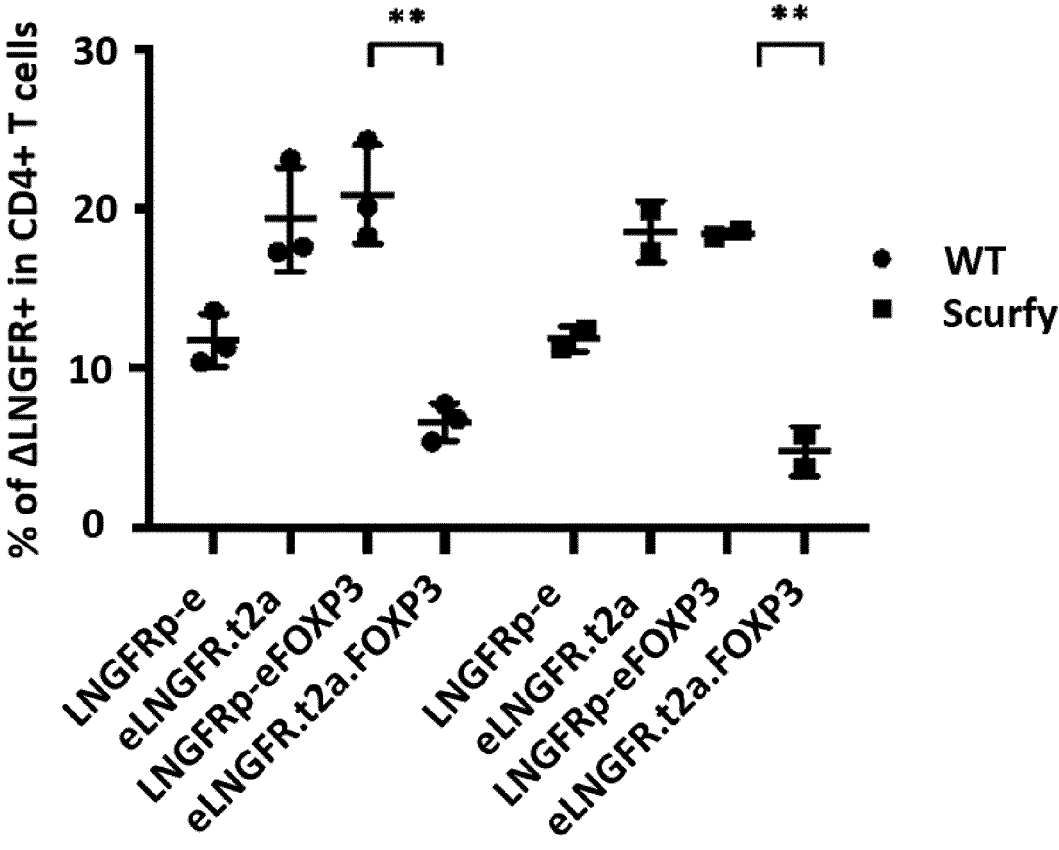

FIG. 3 depicts the transduction efficacy quantified by the percentage of ΔLNGFR at day 5 after transduction in WT and Scurfy CD4+ T cells. Transduction efficiency was significantly increased with LNGFRp-eFOXP3 vector compared to LNGFR.t2a.FOXP3 both for WT and Scurfy CD4+ T cells (with a p-value=0.002 and =0.007 respectively, Mann-Whitney test). On the opposite, transduction efficacy with the mock vectors was higher with the T2A construct with p-value=0.02 and =0.04 respectively in WT and Scurfy CD4+ T cells. (n=3 independent experiment for WT CD4+ T cells and 2 independent experiments for Scurfy CD4+Tc ells).

EXAMPLE

Material and Methods

Mice

Scurfy phenotype was obtained by backcrossing on B6.129S7-Rag1tmlMom/J background, allowing generation of homozygous XSf/XSf.Rag1–/– female. Crossing of these female with WT C57BL/6J mice result in the birth only of diseased XSf/Y.Rag1–/+ male.

WT CD4 T Cells

Splenocytes were harvested from C57BL/6J by aseptic removal. After gentle crushing of spleens through a 70 μM mesh filter, CD4+ T cells were isolated by negative selection using EasySep Mouse CD4+ T cell Isolation Kit (StemCell Technologies, Grenoble, France). Purity exceeded 90%.

Scurfy CD4 T Cells

From XSf/Y.Rag1–/+ mice of 10 days, lymph nodes were collected and CD4+ T cells were separated using Murine CD4+ T cell Isolation kit (Miltenyi Biotec, Paris, France). Briefly, CD4+ collected from lymph nodes were labeled with a cocktail of biotinylated antibodies targeting CD4– cells, followed by labeling with anti-biotin magnetic beads. Cells were separated on an LS column (Miltenyi Biotec) and CD4+ cells were collected in the flow through. Purity exceeded 90%.

WT Tregs CD4+CD25+

Splenocytes and lymph nodes were harvested from B6LY5.1 CD45.1 (8-12 weeks) and CD4+ T cells were isolated using EasySep Mouse CD4+ T cell Isolation Kit. A staining of CD25+ cells was performed with an anti-CD25 PE antibody (clone PC61, BD Biosciences, Le Pont de Claix, France), and then CD4+CD25+ cells were sorted on SH800 (Sony Biotechnology, Weybridge, UK) or ARIA II (BD Biosciences) cells sorters with a nozzle of 100 μm. For Treg suppression assay, CD4+CD25– cells were also sorted.

Lentiviral Vector

The cDNA for a truncated codon-optimized human ΔLNGFR and/or a codon optimized human FOXP3 was cloned in a pCCL backbone with different designs. Bidirectional vector contains ΔLNGFR in a reverse position under the control of respectively PGK or mCMV promoters, FOXP3 is under the control of EF1a promoter. A unidirectional polyA sequence was added to terminate transduction of the reverse gene.

In T2A designs, expression is under the control of EF1a. Two constructs were built: ΔLNGFR followed by the T2A sequence and FOXP3 or FOXP3 followed by the T2A and ΔLNGFR.

Lentiviral vectors were packaged with a VSV-G pseudotype as previously described. Production of bidirectional constructs was increased thanks to co-transfection with NovB2 plasmid26.

T Cell Transduction

Freshly isolated CD4+ T cells were plated at $4.10^6$ cells/mL in round bottom plate in RPMI 1640 medium+GlutaMax (GIBCO, Thermo Fisher Scientific, Montigny-Le-Bretonneux, France) supplemented with 10% fetal bovine serum (GIBCO), 1% Penicillin-Streptomycin (GIBCO), 0.1% 2-mercaptoethanol (GIBCO). Medium was supplemented with recombinant murine IL-2 (Peprotech, Rocky Hill, USA) at a concentration of 100 UI/ml for WT CD4 T cells or 300 UI/ml for Scurfy CD4 T cells. Cells were activated and expanded with anti-CD3/CD28 Dynabeads (GIBCO) at a 1:1 bead:cell ratio. Transduction was performed according the protocol previously described[43] (ref article LB). Briefly transduction medium (RPMI supplemented with 0.25 mg/ml Lentiboost (Sirion Biotech, FlashTherapeutics, Toulouse, France)) was added to cells with lentiviral vector at a MOI 10 concomitantly with activation and incubated overnight. Transduced cells were stained at day 5 after transduction by ΔLNGFR PE antibodies (clone ME20.4-1.H4, Miltenyi Biotec) and sorted on SH800 (Sony Biotechnology).

Determination of Vector Copies Number

Genomic DNA was extracted from samples 10 days after transduction using a Genomic DNA Purification kit (Qiagen, Cergy-Pontoise, France). VCN were quantified using qPCR or ddPCR. qPCR were performed following the protocol previously described[43]. For ddPCR, gDNA were first digested by Hind III HF (New England Biolabs, Evry, France) then mixed with ddPCR Mastermix (Bio-rad, Marnes-la-Coquette, France), primers and probes specific to the HIV Psi region (Bio-Rad) and a sequence in the murine genome (Titin) or human genome (Albumin) for normalization. Droplet generation was performed using the QX100 Droplet. The concentration of specific amplified portions was quantified using the QX200 Droplet Reader/Quantasoft V1.7 (Bio-Rad).

Treg Suppression Assay

Bonafide WT Treg cells (CD4+CD25+) or indicated engineered CD4+ Tcells from Scurfy mice were co-cultured with Tconv (WT CD4+CD25–, 1.104 cells/well) and stimulated with anti-CD3 (1 μg/ml) in the presence of mitomycin C (50 μg/ml) (Merck KGaA) treated splenocytes, 1.104/well) with complete RPMI medium in round-bottom 96-well plates. Treg cells or engineered CD4+ Tcells were labeled with 5 μM Cell trace violet proliferation dye (Thermo Fisher Scientific) whereas Tconv cells were labeled with 5 μM CFSE to differentiate the two populations.

Suppressive cells were co-cultured with Tconv at degressive ratio Treg:Tconv (1:1, 2:1, 4:1, 8:1, 16:1, 32:1, 64:1) for 3 days followed by FACS analysis (MACSquant, Miltenyi Biotec). 7AAD staining was added to remove dead cells. Proliferation index was calculated with FlowJo (BD Biosciences) modelisation.

Flow Cytometry

Single cell suspensions from spleen and lymph nodes were obtained by gentle crushing of spleens through a 70 μM mesh filter. Samples from the lung and the liver were prepared after digestion with Collagenase IV (Thermo Fischer Scientific) followed by gentle crushing of spleens through a 100 μM mesh filter.

Samples were prepared for flow cytometry using the following method: Cells were resus-pended in 100 uL of FACS buffer (phosphate buffered saline (PBS, Corning)/2% Fetal Bovine Serum [GIBCO]) and incubated with 2 uL of each antibody 7AAD (Miltenyi Biotec) for 20-30 min at 4 C.

Cells were washed once in FACS buffer prior to analysis. For intracellular FoxP3 staining, cells were first stained with cell surface markers and fixable viability dye eF780 (eBioscience, Thermo Fischer Scientific) as described above. After washing, cells were fixed and permeabilized using the FoxP3 staining buffer set eBioscience, Thermo Fischer Scientific) according to manufacturers' directions. Human FoxP3-APC (eBioscience, Thermo Fischer Scientific) was added for 30-60 min at RT. Samples were acquired on a MACSquant flow cytometer (Miltenyi Biotec), BD LSR Fortessa cytometer (BD Biosciences) or a Sony Spectral SH6800 (Sony Biotechnology). Data were analyzed using FlowJo V10 (TreeStar). The following antibodies were used: anti-mouse CD62L APC-Cy7 clone MEL-14, CD44APC clone IM7 (BD Biotechnology), CD45.1 APC-Cy7 clone A20, CD45.2 PeCy7 clone 104, CD134 clone OX-40 Brilliant Violet 421, CD279 (PD-1) clone 29F.1A12 Brilliant Violet 605, CD25 clone PC61 Brilliant Violet 711, TIGIT clone Vstm3 1G9 PE, CD357 (GITR) clone DTA-1 PerCP/Cy5.5, CD39 clone Duha59 PE/Cy7 and CD152 clone UC10-4B9 PE/Dazzle (Sony Biotechnology) and human ΔLNGFR PE clone ME20.4-1.H4 (Miltenyi Biotec), Helios clone 22F6 eF450 and human FOXP3 APC Clone PCH101 (eBioscience, Thermo Fischer Scientific)

Histology

Lung, liver and ear was collected after mice euthanasia and fixed in PFA 4% (Sigma). Tissues section was stained with HE and inflammation was analyzed as described by Workman and al. 44.

Statistical Analysis

Values are represented as means±SD, unless stated otherwise. GraphPad Prism 6.0 was used for all statistical analyses. P value was calculated with a confidence interval of 95% to indicate the statistical significance between groups. Statistical test included non-parametric Mann-Whitney test, Fischer exact test or two ways ANOVA depending on the dataset. A P value <0.05 was considered statistically significant. Statistically significant differences between groups are noted in figures with asterisks (*p<0.05, p<0.01, *p<0.001, ****p<0.0001). Correlations were performed with a non-parametric Spearman correlation. Survival was analyzed with Log-rank test (Mantel-Cox).

Ethics

Animal procedure received our institution ethics committee agreement and Ministère de l'Agriculture agreement according to European directive 2010/63/UE.

Results

Example 1

We compared 6 different lentiviral constructs according to 4 criteria (vector titers, level of transduction of human CD4+ T cells, level of expression of FOXP3 and zLNGFR genes, degree of correlation between both expression) (FIG. 1):

91: unidirectional, EFS-FOXP3, PGK-ΔLNGFR
95: unidirectional, PGK-FOXP3, EFS-ΔLNGFR
99: bidirectional, ΔLNGFR-PGK, EF1a-FOXP3
103: bidirectional, ΔLNGFR-mCMV, EF1a-FOXP3
151: bicistronic, EF1a-ΔLNGFR-T2A-FOXP3
155: bicistronic, EF1a-FOXP3-T2A-ΔLNGFR Table 1 below illustrates vector titer, transduction efficiency measured in vector copy number (VCN) per cell at day 12 of culture, and coexpression of FOXP3 and ΔLNGFR measured by flow cytometry indicated as % of CD4+ T cells at day 5. In some cases, ΔLNGFR+ cells were sorted at day 5, further cultured for 12 days and analysed by flow cytometry at D12 (FIG. 2).

expression of FOXP3. To note, the bidirectional construct tested by Passerini and coll (Passerini et al., 2013) that we reproduce herein with the codon optimized version (#103) was not efficient in terms of correlation of expression of FOXP3 and ZLNGFR genes. The only constructs that fulfilled the 4 criteria defined above is the bidirectional designs including forward hFOXP3co under the control of the EF1 promoter and reverse ΔLNGFRco under the control of PGK promoter (#99, pCCL.ΔLNGFRco.PGK.EF1a.hFOXP3co).

Example 2

Figure 1:
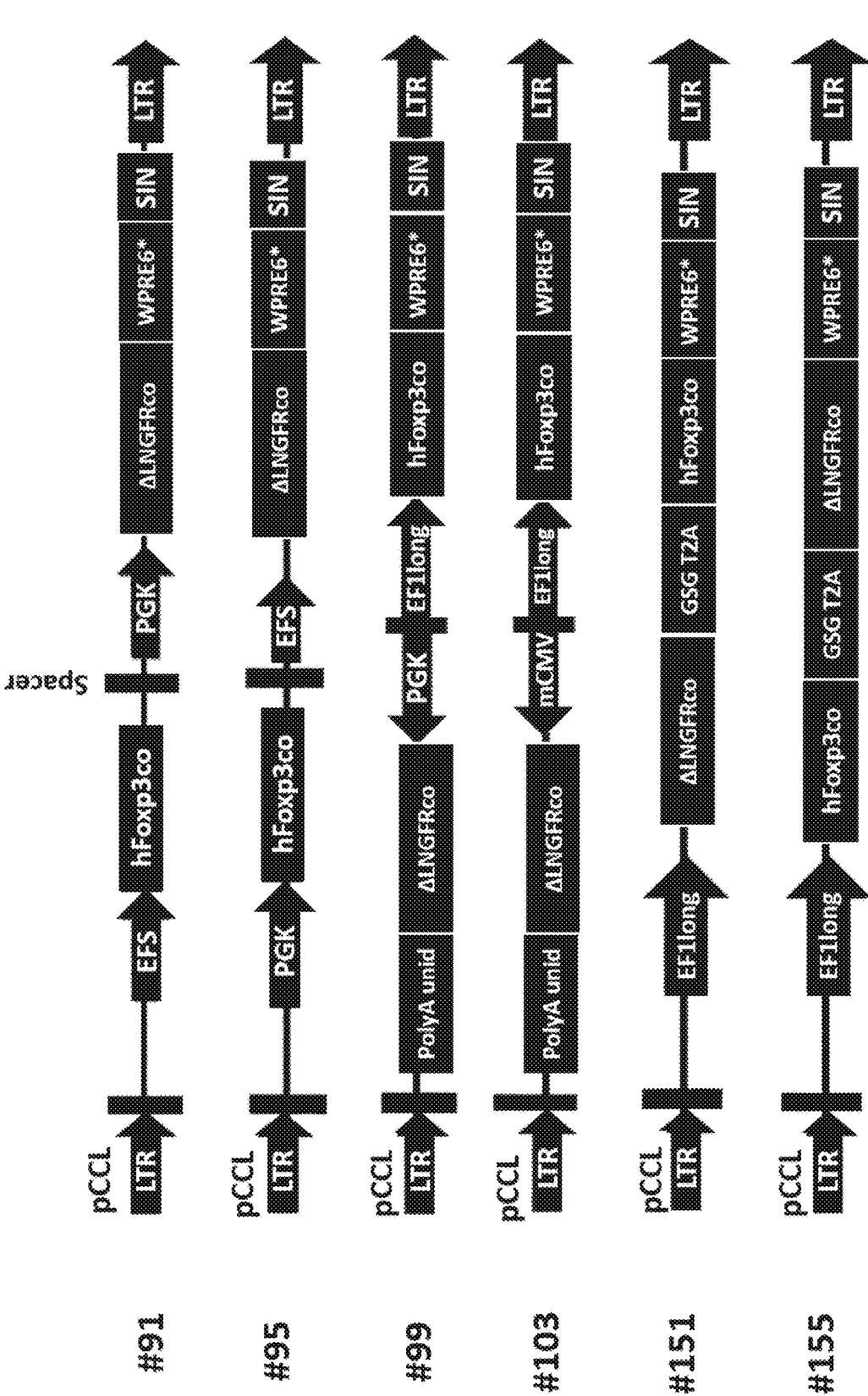
FIG. 1 depicts the different constructions tested by the inventors.

Concomitant expression of two genes, here FOXP3 and ΔLNGFR reporter, can be obtained by either bicistronic construct or bidirectional promoters. We generated vectors (i) one with the bidirectional promoters architecture, one allowing FOXP3 expression under the control of the ubiquitous elongation factor 1 alpha (EF1a) and ΔLNGFR under the control of phosphoglycerate kinase (PGK) human promoter and their mock counterpart containing only the ΔLNGFR reporter (LNGFRp-eFOXP3 and LNGFRp-e, also known as #99) and (ii) two bicistronic using 2A self-cleaving peptide system with their mock counterpart (named eLNGFR.t2a.FOXP3 and eLNGFR.t2a, also known as #151 vs. eFOXP3.t2a.LNGFR and e.t2a.LNGFR, also known #155) (FIG. 1).

With the exception of LNGFRp-e, bidirectional vectors' titers quantified by titration assay were more than 10 fold higher as compared to bicistronic T2A vectors (Table 2).

TABLE 2

| Vectors | Titer (Ig/mL) |
|---|---|
| LNGFRp-e | $1.4 \times 10^8$ |
| LNGFRp-eFOXP3 (#99) | $1.5 \times 10^9$ |
| eLNGFR.t2a | $5.9 \times 10^7$ |
| eLNGFR.t2a.FOXP3 (#151) | $1.1 \times 10^8$ |
| e.t2a.LNGFR | $2.3 \times 10^7$ |
| eFOXP3.t2a.LNGFR (#155) | $6.4 \times 10^7$ |

Despite a bidirectional design the titer was sufficient thanks to the use for production of NovB2 which inhibits the RNA interference mechanism induced by the reverse transcript 26. CD4+ T cell isolated from WT mice were activated with anti-CD3/CD28, IL-2 and simultaneously transduced at a MOI 10 with the 4 constructs and their empty control counterparts. Surface ΔLNGFR and intracellular FOXP3 expressions were evaluated by flow cytometry 5 days after transduction (Data not shown). The level of transduction ranged from 5.2 to 25.2% ΔLNGFR+ cells. Correlation

TABLE 1

| Vector | Titer | VCN (D 12) | % LNGFR+FOXP3+ (D 5) | % LNGFR+FOXP3+ (D 12) after sorting at D 5 |
|---|---|---|---|---|
| #91 | 1.49 × 10e9 | 4 | 13.2 | ND |
| #95 | ND | ND | 9.1 | ND |
| #99 | 1.36 × 10e9 | 1.18 | 32.7 | 83.6 |
| #103 | 1.3 × 10e9 | 0.45 | 11.8 | ND |
| #151 | 2.35 × 10e8 | 0.61 | 25.9 | ND |
| #155 | 6.36 × 10e7 | 0.31 | 20.6 | ND |

Constructs #151 and #155 were excluded because of low titers. #95 and #103 were excluded because of low levels of coexpression of FOXP3 and ZLNGFR genes and low VCN for #103. #91 was excluded because of the low level of between FOXP3 and ΔLNGFR was respectively quantified with Spearman correlation at expression $r^2=0.51$, $r^2=0.54$, $r^2=0.66$ and $r^2=0.61$ respectively for LNGFRp-eFOXP3, eLNGFR.t2a.FOXP3 and eFOXP3.t2a.LNGFR vectors.

eFOXP3.t2a.LNGFR vector was excluded for further evaluation because transduction efficiency was low. Both LNGFRp-eFOXP3 and eLNGFR.t2a.FOXP3 constructs were further tested in Scurfy CD4+ T cells. Scurfy CD4+ T cells are highly sensitive to cell sorting and culture, probably as a consequence of chronically activated environment. Therefore, we first optimized Scurfy CD4+ T cell sorting starting from lymph nodes to limit the contamination by B cells, granulocytes and monocytes and to reach purity above 95%. Viability of Scurfy CD4+T in culture was improved by the selection of donor mice of an age beyond 12 days to limit inflammation and maintained above 80% up to 12 days using 300 UI/mL IL-2 (compared to 100 UI/ml for WT CD4 T cells). As shown in FIG. 3, the level of transduction after 5 days was significantly higher with the bidirectional LNGFRp-eFOXP3 construct as compared to the bicistronic eLNGFR.t2a.FOXP3 construct not only for WT CD4+T lymphocytes, but also for Scurfy CD4+T lymphocytes (p-value=0.002 and 0.007 respectively). Transduced cells were sorted five days after transduction and expanded for 7 supplemental days for VCN quantification. VCN in WT CD4+T lymphocytes ranged between 0.9 and 1.9 for bidirectional design. VCN range was similar in Scurfy mice with bidirectional design ranging between 0.9 and 1.4. The poor viability of Scurfy CD4 cells transduced with T2A vectors did not allow quantification of VNC in those conditions. After 5 days of culture, mean fluorescent intensity of FOXP3 expression was similar between $CD4^{LNGFRp-eFOXP3}$ and $CD4^{eLNGFR.t2a.FOXP3}$ in WT cells but was significantly increased with the bidirectional LNGFRp-eFOXP3 construct in Scurfy CD4+T lymphocytes (p-value=0.04) (Data not shown). Since the three required criteria were achieved (efficient transduction, suitable correlation between FOXP3 and ΔLNGFR expression and stability in vitro), LNGFRp-eFOXP3 and its mock counterpart LNGFRp-e were selected for functional evaluation. They will be named LNGFR.FOXP3 and LNGFR vector thereafter.

Thymic Tregs are defined by a specific combination of surface molecules, which includes particularly CTLA-4 and CD25. At day 7 post transduction, CTLA-4 and CD25 expression was higher in $CD4^{LNGFR.FOXP3}$ transduced cells as compared to $CD4^{LNGFR}$ transduced cells (Data not shown). Functional evaluation of transduced cells was performed using an in vitro suppression assay. ΔLNGFR+ cells were sorted at day 5 post-transduction with either LNGFR.FOXP3 or LNGFR vector. The capacity of sorted cells ($CD4^{LNGFR.FOXP3}$ and $CD4^{LNGFR}$) to suppress proliferation of CFSE labelled CD4+CD25− Tconv was measured at a 1:1 up to 1:64 suppressor-to-effector ratio and compared to that of WT CD4+CD25$^{high}$ Tregs as positive controls, and untransduced Scurfy CD4+ T cells ($CD4^{UT}$) as negative controls (Data not shown). $CD4^{LNGFR}$ and $CD4^{UT}$ resulted in a small level of proliferation inhibition up to ratio 1:4 whereas $CD4^{LNGFR.FOXP3}$ transduced CD4+ T cells were able to suppress Tconv proliferation as well as WT Tregs (up to a suppressor-to-effector ratio of 1:32).

Discussion:

In the present work, we developed a bidirectional lentiviral vector allowing the coexpression of hFOXP3 together with a ΔLNGFR surface reporter. In this study, murine HSPC were collected from Scurfy mice rescued by WT splenocytes injection and transduced. After engraftment in WT mice, corrected CD4 T cells were collected and demonstrated their ability to prevent the onset of Scurfy phenotype. The total number of corrected Scurfy CD4+ T cells injected in Scurfy neonates was ranging between $1.8 \times 10^7$ and $2.5 \times 10^7$ corresponding to a putative Tregs dose ranging between $9.8 \times 10^5$ and $1.4 \times 10^6$ cells. Moreover these results were obtained with high VCN ranging between 3.3 and 5.8. These results demonstrated the feasibility of a HSPC gene therapy but could suggest that the expression of FOXP3 driven by the endogenous promoter might require higher vector copy number and higher cell dose as compared to FOXP3 expression in CD4+ T cells driven by our vector. Our work demonstrated the advantage of a curative strategy based on genetic engineering of CD4+ T cells. The vector we designed allowed inducing a suppressive function in CD4 T cell at lower VCN between 1 and 2. Gene therapy of CD4 T cells with the expression of FOXP3 under the control of an ubiquitous promoter or gene therapy of HSCT with vector allowing the expression of FOXP3 under the control of its own regulated promoter are additive strategies.

REFERENCES

Throughout this application, various references describe the state of the art to which this invention pertains. The disclosures of these references are hereby incorporated by reference into the present disclosure.

Aarts-Riemens, T., M. E. Emmelot, L. F. Verdonck, and T. Mutis. 2008. Forced overexpression of either of the two common human Foxp3 isoforms can induce regulatory T cells from CD4(+)CD25(−) cells. Eur J Immunol 38:1381-1390.

Aiuti, A., R. Bacchetta, R. Seger, A. Villa, and M. Cavazzana-Calvo. 2012. Gene therapy for primary immunodeficiencies: Part 2. Curr Opin Immunol 24:585-591.

Aiuti, A., S. Vai, A. Mortellaro, G. Casorati, F. Ficara, G. Andolfi, G. Ferrari, A. Tabucchi, F. Carlucci, H. D. Ochs, L. D. Notarangelo, M. G. Roncarolo, and C. Bordignon. 2002. Immune reconstitution in ADA-SCID after PBL gene therapy and discontinuation of enzyme replacement. Nat Med 8:423-425.

Allan, S. E., A. N. Alstad, N. Merindol, N. K. Crellin, M. Amendola, R. Bacchetta, L. Naldini, M. G. Roncarolo, H. Soudeyns, and M. K. Levings. 2008. Generation of potent and stable human CD4+T regulatory cells by activation-independent expression of FOXP3. Mol Ther 16:194-202.

Barzaghi, F., L. Passerini, and R. Bacchetta. 2012. Immune dysregulation, polyendocrinopathy, enteropathy, x-linked syndrome: a paradigm of immunodeficiency with auto-immunity. Front Immunol 3:211.

Bennett, C. L., J. Christie, F. Ramsdell, M. E. Brunkow, P. J. Ferguson, L. Whitesell, T. E. Kelly, F. T. Saulsbury, P. F. Chance, and H. D. Ochs. 2001. The immune dysregulation, polyendocrinopathy, enteropathy, X-linked syndrome (IPEX) is caused by mutations of FOXP3. Nat Genet 27:20-21.

Blaese, R. M., K. W. Culver, A. D. Miller, C. S. Carter, T. Fleisher, M. Clerici, G. Shearer, L. Chang, Y. Chiang, P. Tolstoshev, J. J. Greenblatt, S. A. Rosenberg, H. Klein, M. Berger, C. A. Mullen, W. J. Ramsey, L. Muul, R. A. Morgan, and W. F. Anderson. 1995. T lymphocyte-directed gene therapy for ADA-SCID: initial trial results after 4 years. Science 270:475-480.

Bonino, C., G. Ferrari, S. Verzeletti, P. Servida, E. Zappone, L. Ruggieri, M. Ponzoni, S. Rossini, F. Mavilio, C. Traversari, C. Bordignon. 1997. HSV-TK Gene Transfer into Donor Lymphocytes for Control of Allogeneic Graft-Versus-Leukemia. Science 276: 1717-1724.

Bonini, C., M. K. Brenner, H. E. Heslop, and R. A. Morgan. 2011. Genetic modification of T cells. Biol Blood Marrow Transplant 17:S15-20.

Brunkow, M. E., E. W. Jeffery, K. A. Hjerrild, B. Paeper, L. B. Clark, S. A. Yasayko, J. E. Wilkinson, D. Galas, S. F. Ziegler, and F. Ramsdell. 2001. Disruption of a new forkhead/winged-helix protein, scurfin, results in the fatal lymphoproliferative disorder of the scurfy mouse. Nat Genet 27:68-73.

Ferraro, A., A. M. D'Alise, T. Raj, N. Asinovski, R. Phillips, A. Ergun, J. M. Replogle, A. Bernier, L. Laffel, B. E. Stranger, P. L. De Jager, D. Mathis, and C. Benoist. 2014. Interindividual variation in human T regulatory cells. Proc Natl Acad Sci USA 111:E1111-1120.

Fontenot, J. D., M. A. Gavin, and A. Y. Rudensky. 2003. Foxp3 programs the development and function of CD4+ CD25+ regulatory T cells. Nat Immunol 4:330-336.

Fu, W., A. Ergun, T. Lu, J. A. Hill, S. Haxhinasto, M. S. Fassett, R. Gazit, S. Adoro, L. Glimcher, S. Chan, P. Kastner, D. Rossi, J. J. Collins, D. Mathis, and C. Benoist. 2012. A multiply redundant genetic switch 'locks in' the transcriptional signature of regulatory T cells. Nat Immunol 13:972-980.

Hori, S., T. Nomura, and S. Sakaguchi. 2003. Control of regulatory T cell development by the transcription factor Foxp3. Science 299:1057-1061.

Horino, S., Y. Sasahara, M. Sato, H. Niizuma, S. Kumaki, D. Abukawa, A. Sato, M. Imaizumi, H. Kanegane, Y. Kamachi, S. Sasaki, K. Terui, E. Ito, I. Kobayashi, T. Ariga, S. Tsuchiya, and S. Kure. 2014. Selective expansion of donor-derived regulatory T cells after allogeneic bone marrow transplantation in a patient with IPEX syndrome. Pediatr Transplant 18:E25-30.

Kalos, M., and C. H. June. 2013. Adoptive T cell transfer for cancer immunotherapy in the era of synthetic biology. Immunity 39:49-60.

Kasow, K. A., V. M. Morales-Tirado, D. Wichlan, S. A. Shurtleff, A. Abraham, D. A. Persons, and J. M. Riberdy. 2011. Therapeutic in vivo selection of thymic-derived natural T regulatory cells following non-myeloablative hematopoietic stem cell transplant for IPEX. Clin Immunol 141:169-176.

Khattri, R., T. Cox, S. A. Yasayko, and F. Ramsdell. 2003. An essential role for Scurfin in CD4+CD25+T regulatory cells. Nat Immunol 4:337-342.

Li, W., L. Wang, H. Katoh, R. Liu, P. Zheng, and Y. Liu. 2011. Identification of a tumor suppressor relay between the FOXP3 and the Hippo pathways in breast and prostate cancers. Cancer Res 71:2162-2171.

Masiuk K E, Laborada J, Roncarolo M G, Hollis R P, Kohn D B. Lentiviral Gene Therapy in HSCs Restores Lineage-Specific Foxp3 Expression and Suppresses Autoimmunity in a Mouse Model of IPEX Syndrome. Cell Stem Cell. 2019; 24(2):309-317.e7. doi:10.1016/j.stem.2018.12.003

Mottet, C., H. H. Uhlig, and F. Powrie. 2003. Cutting edge: cure of colitis by CD4+CD25+ regulatory T cells. J Immunol 170:3939-3943.

Muul, L. M., L. M. Tuschong, S. L. Soenen, G. J. Jagadeesh, W. J. Ramsey, Z. Long, C. S. Carter, E. K. Garabedian, M.

Alleyne, M. Brown, W. Bernstein, S. H. Schurman, T. A. Fleisher, S. F. Leitman, C. E. Dunbar, R. M. Blaese, and F. Candotti. 2003. Persistence and expression of the adenosine deaminase gene for 12 years and immune reaction to gene transfer components: long-term results of the first clinical gene therapy trial. Blood 101:2563-2569.

Passerini, L., E. Rossi Mel, C. Sartirana, G. Fousteri, A. Bondanza, L. Naldini, M. G. Roncarolo, and R. Bacchetta. 2013. CD4(+) T cells from IPEX patients convert into functional and stable regulatory T cells by FOXP3 gene transfer. Sci Transl Med 5:215ra174.

Provasi, E., P. Genovese, A. Lombardo, Z. Magnani, P. Q. Liu, A. Reik, V. Chu, D. E. Paschon, L. Zhang, J. Kuball, B. Camisa, A. Bondanza, G. Casorati, M. Ponzoni, F. Ciceri, C. Bordignon, P. D. Greenberg, M. C. Holmes, P. D. Gregory, L. Naldini, and C. Bonini. 2012. Editing T cell specificity towards leukemia by zinc finger nucleases and lentiviral gene transfer. Nat Med 18:807-815.

Sawant, D. V., and D. A. Vignali. 2014. Once a Treg, always a Treg? Immunol Rev 259:173-191.

Seidel, M. G., G. Fritsch, T. Lion, B. Jurgens, A. Heitger, R. Bacchetta, A. Lawitschka, C. Peters, H. Gadner, and S. Matthes-Martin. 2009. Selective engraftment of donor CD4+25high FOXP3-positive T cells in IPEX syndrome after nonmyeloablative hematopoietic stem cell transplantation. Blood 113:5689-5691.

Tang, Q., K. J. Henriksen, M. Bi, E. B. Finger, G. Szot, J. Ye, E. L. Masteller, H. McDevitt, M. Bonyhadi, and J. A. Bluestone. 2004. In vitro-expanded antigen-specific regulatory T cells suppress autoimmune diabetes. J Exp Med 199:1455-1465.

Thornton, A. M., and E. M. Shevach. 1998. CD4+CD25+ immunoregulatory T cells suppress polyclonal T cell activation in vitro by inhibiting interleukin 2 production. J Exp Med 188:287-296.

Trzonkowski, P., M. Bieniaszewska, J. Juscinska, A. Dobyszuk, A. Krzystyniak, N. Marek, J. Mysliwska, and A. Hellmann. 2009. First-in-man clinical results of the treatment of patients with graft versus host disease with human ex vivo expanded CD4+CD25+CD127– T regulatory cells. Clin Immunol 133:22-26.

Wieckiewicz, J., R. Goto, and K. J. Wood. 2010. T regulatory cells and the control of alloimmunity: from characterisation to clinical application. Curr Opin Immunol 22:662-668.

Wildin, R. S., F. Ramsdell, J. Peake, F. Faravelli, J. L. Casanova, N. Buist, E. Levy-Lahad, M. Mazzella, O. Goulet, L. Perroni, F. D. Bricarelli, G. Byrne, M. McEuen, S. Proll, M. Appleby, and M. E. Brunkow. 2001. X-linked neonatal diabetes mellitus, enteropathy and endocrinopathy syndrome is the human equivalent of mouse scurfy. Nat Genet 27:18-20.

Yagi, H., T. Nomura, K. Nakamura, S. Yamazaki, T. Kitawaki, S. Hori, M. Maeda, M. Onodera, T. Uchiyama, S. Fujii, and S. Sakaguchi. 2004. Crucial role of FOXP3 in the development and function of human CD25+CD4+ regulatory T cells. Int Immunol 16:1643-1656.

The invention claimed is:

1. A method of producing a population of Treg cells, comprising the step of transfecting or transducing a population of T cells in vitro or ex vivo with a lentiviral vector comprising a recombinant nucleic acid molecule, wherein the recombinant nucleic acid molecule comprises a bidirectional PGK-EF1a promoter operably linked to a first transgene in one direction and to a second transgene in the opposite direction, wherein the bidirectional PGK-EF1a promoter comprises a nucleic acid sequence as set forth in SEQ ID NO:5, and wherein the first transgene is under control of the first PGK portion of the bidirectional PGK-EF1a promoter and encodes for a truncated low-affinity nerve growth factor receptor (LNGFR) comprising a nucleic acid sequence as set forth in SEQ ID NO: 8, and the second transgene is under control of the second EF1a portion of the bidirectional PGK-EF1a promoter and encodes for FoxP3.

2. A population of Treg cells obtainable by the method of claim 1.

3. The method of claim 1, wherein the sequences of the first transgene and the second transgene are codon-optimized.

4. The method of claim 1, wherein the second transgene comprises a nucleic acid sequence having at least 80% of identity with the nucleic acid sequence as set forth in SEQ ID NO:7.

5. The method of claim 1, wherein the recombinant nucleic acid molecule comprises a nucleic acid sequence having at least 80% of identity with the nucleic acid sequence as set forth in SEQ ID NO:11.

6. The method of claim 1, wherein the recombinant nucleic acid molecule comprises a nucleic acid sequence as set forth in SEQ ID NO:11.

* * * * *